US009593093B2

(12) United States Patent
Mullen et al.

(10) Patent No.: US 9,593,093 B2
(45) Date of Patent: Mar. 14, 2017

(54) METHODS FOR THE MANUFACTURE OF ACETALS AND KETALS, AND THE ACETALS AND KETALS PRODUCED THEREBY

(71) Applicant: SEGETIS, INC., Gloden Valley, MN (US)

(72) Inventors: Brian D. Mullen, Delano, MN (US); Marc D. Scholten, Saint Paul, MN (US); Andrew J. Louwagie, Golden Valley, MN (US); Steven A. Donen, Chanhassen, MN (US); Feng Jing, Snellvile, GA (US); Vivek Badarinarayana, St. Louis Park, MN (US)

(73) Assignee: GFBIOCHEMICALS LIMITED, Valletta (MT)

( * ) Notice: Subject to any disclaimer, the term of this patent is extended or adjusted under 35 U.S.C. 154(b) by 0 days.

(21) Appl. No.: 14/550,222

(22) Filed: Nov. 21, 2014

(65) Prior Publication Data
US 2015/0080585 A1    Mar. 19, 2015

Related U.S. Application Data

(63) Continuation of application No. 13/197,593, filed on Aug. 3, 2011, now abandoned.

(60) Provisional application No. 61/370,365, filed on Aug. 3, 2010.

(51) Int. Cl.
C07D 317/30    (2006.01)

(52) U.S. Cl.
CPC .......... *C07D 317/30* (2013.01); *Y02P 20/582* (2015.11)

(58) Field of Classification Search
CPC ........................... C07D 317/30; Y02P 20/582
IPC .................................................... Y02P 20/582
See application file for complete search history.

(56) References Cited

U.S. PATENT DOCUMENTS

| 1,934,309 | A | 10/1927 | Hoover |
| 2,008,720 | A | 7/1935 | Lawson |
| 2,260,261 | A | 10/1941 | Morey et al. |
| 2,654,723 | A | 10/1953 | Greene |
| 2,556,135 | A | 6/1954 | Croxall et al. |
| 3,658,789 | A | 4/1972 | Fried |
| 4,465,866 | A | 8/1984 | Takaishi et al. |
| 4,792,411 | A | 12/1988 | Walsh |
| 4,923,891 | A | 5/1990 | Deason et al. |
| 5,095,098 | A | 3/1992 | McLain et al. |
| 5,202,413 | A | 4/1993 | Spinu |
| 5,266,592 | A | 11/1993 | Grub et al. |
| 5,917,059 | A | 6/1999 | Bruchmann et al. |
| 5,998,092 | A | 12/1999 | McCulloch et al. |
| 6,528,025 | B1 | 3/2003 | Boesch et al. |
| 6,806,392 | B2 | 10/2004 | Boesch et al. |
| 6,828,272 | B2 | 12/2004 | Wiegner et al. |
| 7,553,819 | B2 | 6/2009 | Bundle et al. |
| 7,968,563 | B2 | 6/2011 | Kshirsagar et al. |
| 8,053,468 | B2 | 11/2011 | Selifonov |
| 8,575,367 | B2 | 11/2013 | Selifonov et al. |
| 8,604,077 | B2 | 12/2013 | Wicks et al. |
| 8,604,223 | B2 | 12/2013 | Selifonov et al. |
| 8,829,229 | B2 | 9/2014 | Tulchinsky et al. |
| 2003/0167681 | A1 | 9/2003 | Delgado Puche |
| 2004/0024260 | A1 | 2/2004 | Winkler et al. |
| 2005/0210738 | A1 | 9/2005 | Manzer |
| 2006/0063948 | A1 | 3/2006 | Manzer |
| 2007/0015792 | A1 | 1/2007 | Hashimoto et al. |
| 2007/0123741 | A1 | 5/2007 | Van Der Puy et al. |
| 2010/0273824 | A1 | 10/2010 | Sorensen et al. |

FOREIGN PATENT DOCUMENTS

| CA | 1000285 | 11/1976 |
| DE | 10036423 A1 | 3/2001 |
| FR | 1445013 | 7/1966 |
| JP | 4217972 A | 8/1992 |
| JP | 2006143702 A | 6/2006 |
| SU | 722912 | 3/1980 |
| WO | 9412489 A1 | 6/1994 |
| WO | 2008098375 A1 | 8/2008 |

(Continued)

OTHER PUBLICATIONS

Showler et al., "Condensation Products of Glycerol with Aldehydes and Ketones. 2-Substituted m-Dioxan-5-OLS and 1,3-dioxolane-4-methanols," Chem. Rev. 1967, 67 (4), pp. 427-440.
Smith et al., "The gem-Dialkyl Effect. III. Kinetic and Equilibrium Studies of Steroid Cyclic Ketal Formation and Hydrolysis", Journal of the American Chemical Society (1968) 90(5): pp. 1253-1257.
Smith, "Chemical Process Design and Integration", Centre for Process Integration, School of Chemical Engineering and Analytical Science, Univ. of Manchester, John Wiley & Sons, Ltd., 2005, 85 pages, Chapters 7, 11, and 13.
Stern et al., "On Hydroboration of 5-Dimethylamino-3-Methyl-1-Pentene and 5-Dimethylamino-3,3-Dimethyl-1-Pentene", Collection Czechoslov. Chem. Commun., vol. 39, (1974), pp. 3538-3547.
Tang, "Synthesis and Application of Fructone", Contemporary Chemical Industry, vol. 38, No. 3, Jun. 30, 2009, pp. 312-314, with English abstract.

(Continued)

*Primary Examiner* — Samantha Shterengarts
*Assistant Examiner* — Matt Mauro
(74) *Attorney, Agent, or Firm* — Cantor Colburn LLP

(57) ABSTRACT

A method for producing a product that comprises glycerol ketal of ethyl levulinate or propylene glycol ketal of ethyl levulinate comprises reacting either glycerol or propylene glycol with ethyl levulinate in the presence of a homogenous or heterogeneous catalyst system in a reactor system. The ethyl levulinate and either glycerol or propylene glycol are heated to remove water, polyol, and excess ethyl levulinate. The excess ethyl levulinate and polyol is recycled back to the reactor. The product is distilled in a specific fashion and optionally treated by means of a stabilizing agent or acid species removal bed, to obtain a composition comprising glycerol ketal of ethyl levulinate or propylene glycol ketal of ethyl levulinate wherein the composition comprises less than or equal to about 2 wt % contaminants.

33 Claims, 3 Drawing Sheets

(56) References Cited

FOREIGN PATENT DOCUMENTS

| WO | WO 2009/048874 | * | 4/2009 |
| WO | 2011140644 A1 | | 11/2011 |

OTHER PUBLICATIONS

Wang et al., "An efficient procedure for protection of carbonyls catalyzed by sulfamic acid", Journal of Molecular Catalysis A: Chemical 233 (2005), pp. 121-126.
Wedmid et al., "Long-Chain Stereomeric 2-Alkyl-4-methoxycarbonyl-1,3-dioxolanes in Glycerol Acetal Synthesis", J. Org. Chem. 42(22), (1977), pp. 3624-3626.
Wood et al., "Cyclic polyesters: 1. Preparation by a new synthetic method, using polymer-supported reagants", Polymer 34 (14): (1993) pp. 3052-3058.
Written Opinion for International Application No. PCT/US2008/079083, Application Filing Date Oct. 7, 2008, Date of Mailing Jan. 22, 2009, 6 pages.
Xu et al., "The use of polymer supports in organic synthesis. XXVIII. The monoblocking of symmetrical diketones on insoluble polymer supports", Canadian Journal of Chemistry, vol. 61, No. 7, (1983), pp. 1405-1409.
Yamaguchi, "Synthesis of polycyclic aromatic compounds via polyketides", Yuki Gosei Kagaku Kyokaishi, vol. 45, No. 10, (1987), pp. 969-982, with English Abstract.
Yang et al., "Investigation of homopolymerization rate of perfluoro-4,5-substituted-2-methylene-1,3-dioxolane derivatives and properties of the polymers", Journal of Flourine Science 127, (2006), pp. 277-281.
Zhang et al., "Synthesis of Ketals of 4-Oxopentanoates," Lanzhou Daxue Xuebao, Ziran Kexueban 30(2), (1994), pp. 66-70, with English Abstract.
Atofina Publication No. A-70-1 ( © 2001 by Atofina Chemicals, Inc. of Philadelphia, PA; available on the internet at http://staging.arkemainc.com/literature/pdf/405.pdf, 5 pages.
Boehm et al., "Knowledge on cyclic ketals. Part 11: Synthesis of some new derivatives and separation of their isomers", Pharmazie 36 (5), (1981), 3 pages.
Brigl, Percy, et al., "The Reaction of the Pyruvic Acid with Glycerin," Annalen der Chemie 476: p. 215-232, Received Oct. 7, 1929, (with English translation).
Calinaud et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide", Carbohydrate Res. 30(1) 1973 Abst Only.
Carey et al., "Advanced Organic Chemistry, Second Edition, Part B: Reactions and Synthesis", Plenum Press, NY (1983) pp. 539-552.
Chirila, Pent- and hexatomic cycloacetal esters. Synthesis and characterization of some 2-Carbalkoxymethyl-1,3-dioxolanes (dioxanes), Revista de Chimie, Aug. 1977, vol. 28, pp. 730-733; with Human Translation, 20 pages.
Chopade et al., "Acetalization of ethylene glycol with formaldehyde using cation-exchange resins as catalysts: batch versus reactive distillation", Reactive & Functional Polymers 34 (1997) pp. 37-45.
Clarkson et al., "Continuous Reactor Technology for Ketal Formation: An Improved Synthesis of Solketal", Organic Process Research & Development, 5, 2001, pp. 630-635.
Clerici et al., "Efficient Acetalisation of Aldehydes Catalyzed by Titanium Tetrachloride in a Basic Medium", Tetrahedron 54, (1998), pp. 15679-15690.
Cuiling et al., "Synthesis of Levulinic Ketals with Furfuryl Alcohol as Raw Material", Journal of Huagiao University (Nature Science) 23 (3), Jul. 2002, pp. 257-259, with English Translation, 8 pages.
Daignault et al., "2-Cyclohexyloxyethanol [Ethanol, 2-(cyclohexyloxy)-]", Organic Syntheses, 37, 2003, pp. 303-306, XP009176527.
Deslongchamps, Pierre, et al., "The total synthesis of (+)-ryanodol. Part II. Model studies for rings B and C of (+)-anhydroryandol.

Preparation of a key Pentacyclic intermediate", Can. J. Chem. 68 (1990) p. 127-152.
Deutsch, et al., Investigations on heterogeneously catalysed condensations of glycerol to cyclic acetals, Journal of Catalysis 245: 428-435 (2007).
Di Serio, et al., Transesterification of Soybean Oil to Biodiesel by Using Heterogeneous Basic Catalysts, Ind. Eng. Chem. Res. 45: 3009-3014 (2006).
DOW Product Data Sheet, "Amberlite IR120H", obtained from http://www.dow.com/assets/attachments/business/ier/ier_for_industrial_water_treatment/amberlite_ir120_h/tds/amberlite_ir120_h.pdf on Mar. 9, 2012, 1 page.
DuPont Tyzor Organic Titanates Technical Note—Direct Esterification, E.I. du Pont de Nemours and Company, (2001), 3 pages.
DuPont Tyzor Organic Titanates Technical Note—Transesterification, E.I. du Pont de Nemours and Company, 2001, 3 pages.
European Search Report for European Application No. 08 836 866.7-1462, mailed Mar. 13, 2014, 6 pages.
Extended European Search Report for European Application No. 11815279.2-1462 PCT/US2011/046463, mailed Dec. 4, 2013, 13 pages.
Gasparrini, F., "Synthesis of Dimethyl Acetals, Diethyl Acetals, and Cyclic Acetals Catalyzed by Aminopropylated Silica Gel Hydrocholoride(APSG-HCL)", Tetrahedron 40(9), (1984) p. 1491-1500.
Gelas, et al., "Synthese du 4-oxo et de 4-hydroxy-3,6,8-trioxabicyclo[3.2.1]octanes," Carbohydrate Research 30(1): 21-34 (1973) (with English abstract).
Grosu, et al., "Stereochemistry and NMR Spectra of Some New Unsymmetrical Substituted 2,2-Dialkyl-1,3-Dioxanes," Revue Roumaine de Chimie 41(3-4): 259-263 (1996).
Gutsche, et al., "Reactions of Ethyl Diazoacetate with Aromatic Compounds Containing Hetero Atoms Attached to the Benzyl Carbon," J. Am. Chem. Soc. 76: 2236-2240 (1954).
Haskelbhrg, L., "The preparation of glycerol esters of amino acids," Compt. rend. 190270-190272 (1930).
Hegde, et al., "The Kinetics and Thermodynamics of Bicyclic Ketal Formation: An Application to the Synthesis of the Zaragozic Acids," Tetrahedron 53(32): 11179-11190 (1997).
Hoydonckx, et al., "Esterification and transesterification of renewable chemicals," Topics in Catalysis 27(1-4): 83-96 (2004).
Imwinkelried et al., "Diisopropyl (2S,3S)-2,3-O,Isoprophylidenetartrate", Organic Syntheses, Coll. vol. 8, p. 201 (1993); vol. 65, p. 230 (1987).
International Preliminary Report on Patentability and Written Opinion for International Application PCT/US2011/046463, Application Filing Date Aug. 3, 2011, IPRP Issue Date Feb. 5, 2013, WO Date of Mailing Mar. 9, 2012, 8 pages.
International Preliminary Report on Patentability for International Application No. PCT/US2008/079083, Application Filing Date Oct. 7, 2008, Date of Mailing Jan. 12, 2010, 16 pages.
International Search Report for International Application No. PCT/US2008/07983, Application Filing Dated Oct. 7, 2008, Date of Mailing Jan. 22, 2009, 3 pages.
International Search Report for International Application No. PCT/US2011/046463, Application Filing Date Aug. 3, 2011, Date of Mailing Mar. 9, 2012, 6 pages.
Kaihara et al., "Synthesis and Properties of Poly[poly(ethylene glycol)-co-cyclic acetal] Based Hydrogels", Macromolecules, 40, 2007, pp. 7625-7632.
Li, et al., "Montmorillonite Clay Catalysis. Part 2. An Efficient and Convenient Procedure for the Preparation of Acetals Catalysed by Montmorillonite K-10," J. Chem Research (S) 26-27 (1997).
Lukes, Robert M., Preparation of Methyl Esters Containing the 1,3-Dioxane or 2,4,8,10-Tetroxaspiro[5.5]undecane Structure by Ketal Exchange, 26: 2515-2518 (1961).
March, J. March's Advanced Organic Chemistry, 6th Edition, 2007, Chapter 19, p. 1787-1788.
Meher, et al., "Technical aspects of biodiesel production by transesterification—a review," RSER 194: pp. 1-21 (2004).
Meltzer, et al., "2,2-Disubstituted 1,3-Dioxolanes and 2,2-Disubstituted 1,3-Dioxanes," JOC 25: 712-715 (1960).

(56) References Cited

OTHER PUBLICATIONS

Meskens, Frans A. J., Methods for the Preparation of Acetals from Alcohols or Oxiranes and Carbonyl Compounds, Synthesisn (1981) 501-522.

Miller, et al., "Biorenewable Fuels and Chemicals via Reactive Distillation," Midtech Midland, May 11, 2006 ( Powerpoint Presentation) 17 pages.

Mullen, Brian D., et al., "Catalytic Selectiivity of Ketalization Versus Transesterification", Topics in Catalysis, Kluwer Academic Publishers-Plenum Publishers, NE, vol. 53, No. 15-18, May 28, 2010, pp. 1235-1240.

Nagata et al., "Synthesis and Applications of [2-Methyl-2(oxoalkyl)-1,3-dioxolan-4-yl] methyl Acrylates for Photocrosslinking Agent", Osaka Kogyo Gijutsu Shikensho Kiho 37(1): 8-16 (1986); with English Abstract.

Nakamura et al. "Study on Ketalization Reaction of Poly(vinyl alcohol) by Ketones.IX.Kinetic Study on Acetalization and Ketalization Reaction of 1,3-Butanediol as a Model Compound for Poly(vinyl alcohol)",J.Polym.Sci A: Polym Chem35, pp. 1719-1731, 1997.

Newman et al., "Kinetic and Equilibrium Studies of Cyclic Ketal Formation and Hydrolysis", J. Am. Chem. Soc., 1958, 80 (23), pp. 6350-6355.

Oku et al., "Three- and Four-Carbon Elongating Ring Expansion of Cyclic Acetals to Medium-Sized Dioxacycloalkenones. Use of the Intramolecular Formation of Oxonium Ylides", J. Org. Chem, 1997, 62, pp. 2123-2129.

Ono et al., "Preparation, Surface-Active Properties and Acid Decomposition Profiles of a New 'Soap' Bearing a 1,3-Dioxolane Ring", JAOCS, vol. 70, No. 1, 1993, pp. 29-36.

Otera, "Esterificaton: Methods, Reactions, and Applications", Wiley-VCH Verlag GmbH & Co., (2003) 19 pages.

Otera, "Esterificaton: Methods, Reactions, and Applications", Wiley-VCH Verlag GmbH & Co., (2010), 49 pages.

Pasto et al., "Neighboring Group Participation by Carbonyl Oxygen", J. Amer. Chem. Soc., 87(7) (1965) pp. 1515-1521.

Patel et al., "Ketalization of ketones with diols catalyzed by metal (IV) phosphates as solid acid catalysts," Journal of Molecular Catalysis A: Chemical 194: (2003) pp. 267-271.

Piantadosi et al., "The Preparation of Cyclic Glycerol Acetals by Transacetalation," J. Am. Chem. Soc., 1958, 80(24), pp. 6613-6617.

\* cited by examiner

METHODS FOR THE MANUFACTURE OF ACETALS AND KETALS, AND THE ACETALS AND KETALS PRODUCED THEREBY

CROSS-REFERENCE TO RELATED APPLICATIONS

This application is a continuation of U.S. application Ser. No. 13/197,593, filed on Aug. 3, 2011, which claims priority to U.S. Provisional Application No. 61/370,365, filed on Aug. 3, 2010, all of the foregoing being incorporated by reference in their entirety herein.

TECHNICAL FIELD

This disclosure relates to methods for the preparation of acetals and ketals by the acid-catalyzed reaction of alcohols with semialdehydes, ketoacids, and esters thereof.

BACKGROUND

Semialdehydes, ketoacids, and their esters contain an aldehyde or keto group, respectively, in addition to a carboxylic acid or a carboxylic ester group. Reaction of a diol with the aldehyde of a semialdehyde leads to acetal formation, while reaction of the keto group of a ketoacid leads to ketal formation. Diols having a 1,2 hydroxyl group configuration (such as 1,2-ethane diol (ethylene glycol)) will form a dioxolane and diols having a 1,3 hydroxyl group configuration (such as 1,3 propanediol (propylene glycol)) will form a dioxane group. Higher polyols, such as triols and tetrols, including polymeric polyols, can be used to form cyclic ketals as well when at least two of the polyol hydroxyl groups are in the 1,2 or 1,3 configuration.

Acetalization and ketalization is generally carried out in the presence of an acid catalyst, for example a homogeneous, protic acid catalyst such as sulfuric acid, hydrochloric acid, phosphoric acid, p-toluenesulfonic acid and the like.

SUMMARY

While a variety of methods for acetalization and ketalization have been reported, a number of challenges remain, particularly with respect to the large-scale production. For example, one challenge associated with acetalization and ketalization is selective reaction with the aldehyde or keto groups, rather than the oxo group of the carboxylic acid or ester, i.e., esterification and transesterification, which also occurs in the presence of an acid catalyst. Particularly on large scale, it is difficult to obtain highly pure product essentially free of transesterification products or other byproducts There accordingly remains a need in the art for methods for the manufacture of acetals and ketals with high selectivity for acetalization or ketalization over esterification or transesterification reactions. There further remains a need for methods that yield the desired product in high yield and of high purity, that is, free of other side products or contaminants. It would further be desirable to produce products of very low color, particularly have color stability over time. It would further be desirable to produce products that display good shelf stability over time. It would be further advantageous if such methods were cost effective and amenable to large-scale production.

Disclosed herein is a method for the manufacture of a glycerol ketal of ethyl levulinate, the method comprising contacting glycerol with ethyl levulinate and a catalyst in a reactor under reaction conditions to produce a product that comprises a glycerol ketal of ethyl levulinate; fractionating the product under fractionation conditions to separate fractionated materials from the product until the product comprises less than 1000 parts per million of glycerol; recycling the fractionated materials back to the reactor; and distilling the product under distillation conditions wherein the resulting product comprises the glycerol ketal of ethyl levulinate and less than or equal to about 2 wt % contaminants; wherein the contaminants comprise one or more of glycerol, acid species, ethyl levulinate, water, or a high molecular weight byproduct having molecular weights that are at least 1.5 times greater than the molecular weight of the glycerol ketal of ethyl levulinate.

Disclosed herein too is a method for the manufacture of a glycerol ketal of ethyl levulinate, the method comprising contacting glycerol, ethyl levulinate, and a camphor sulfonic acid in a first reactor under a first set of reaction conditions to produce a product that comprises a glycerol ketal of ethyl levulinate; continuously sending the product from the first reactor to a second reactor that is downstream of the first reactor and subjecting the product to a second set of reaction conditions; continuously sending the product from the second reactor to a third reactor that is downstream of the second reactor and subjecting the product to a third set of reaction conditions; thereafter fractionating the product under a set of fractionation conditions to separate fractionated materials from the product until the product comprises less than 1000 ppm of glycerol as measured by GC-FID; and distilling the product in a distillation column under a set of distillation conditions a, wherein the resulting product comprises the glycerol ketal of ethyl levulinate and less than or equal to about 2 wt % contaminants; wherein the contaminants comprise one or more of glycerol, acid species, ethyl levulinate, water, or a high molecular byproduct having molecular weights that are at least 1.5 times greater than the molecular weight of the glycerol ketal of ethyl levulinate.

Disclosed herein too is a method for manufacturing a propylene glycol ketal of ethyl levulinate, the method comprising contacting propylene glycol with ethyl levulinate and a homogenous acid catalyst in a reactor under reaction conditions to produce a product that comprises a propylene glycol ketal of ethyl levulinate; thereafter fractionating the product under fractionation conditions to separate fractionated materials from the product until the product comprises less than 1000 ppm of ethyl levulinate; recycling the fractionated materials back to the reactor; and distilling the product under distillation conditions, wherein the resulting product comprises the propylene glycol ketal of ethyl levulinate and less than or equal to about 2 wt % contaminants; wherein the contaminants comprise one or more of propylene glycol, acid, ethyl levulinate, water, or a high molecular weight byproduct having molecular weights that are at least 1.1 times greater than the molecular weight of the propylene glycol ketal of ethyl levulinate.

Disclosed herein too is a method for manufacturing a propylene glycol ketal of ethyl levulinate, the method comprising contacting propylene glycol with ethyl levulinate and camphor sulfonic acid in a first reactor under a first set of reaction conditions to produce a product that comprises propylene glycol ketal of ethyl levulinate; continuously sending the product from the first reactor to a second reactor that is downstream of the first reactor and subjecting the product to a second set of reaction conditions; continuously sending the product from the second reactor to a third reactor that is downstream of the second reactor and subjecting the product to a third set of reaction conditions; thereafter fractionating the product under a set of fractionation conditions to separate fractionated materials from the product until the product comprises less than 1000 ppm of ethyl levulinate as measured by GC-FID; and distilling the product in a distillation column under a set of distillation conditions, wherein the resulting product comprises the propylene glycol ketal of ethyl levulinate and less than or equal to about 2 wt % contaminants; wherein the contaminants comprise one or more of propylene glycol, acid, ethyl levulinate, water, or a high molecular weight byproduct having molecular weights that are at least 1.1 times greater than the molecular weight of the propylene glycol ketal of ethyl levulinate.

Disclosed herein too is a composition comprising a ketal adduct having the structure (6):

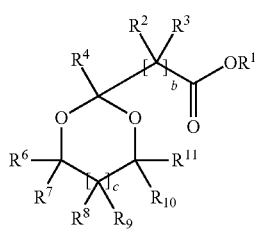

(6)

where $R^1$, $R^2$, $R^3$, and $R^4$ is independently a hydrogen, C1-12 alkyl, C3-6 cycloalkyl, C1-12 alkenyl, C6-12 aryl, C7-13 arylalkyl, or C7-13 alkylaryl, and b is 1-4, $R^5$ is a C1-12 alkyl, C3-6 cycloalkyl, C2-12 alkenyl, C2-12 alkynyl, C6-12 aryl, C7-13 arylalkyl, or C7-13 alkylaryl, each of which can optionally be substituted with one or more addition hydroxyl groups, $R^6$, $R^7$, $R^{10}$, and $R^{11}$ is independently a hydrogen, C1-12 alkyl, C1-12 hydroxyalkylene, C1-12 alkyl substituted with up to six hydroxy groups, C3-6 cycloalkyl, C2-5 heterocycloalkyl, C1-12 alkenyl, C1-12 hydroxyalkenyl, C6-12 aryl, C7-13 arylalkyl, or C7-13 alkylaryl, each $R^8$ and $R^9$ is independently a hydrogen, hydroxyl, C1-12 alkyl, C1-12 hydroxyalkyl, C3-6 cycloalkyl, C1-12 alkenyl, C1-12 hydroxyalkenylene, C6-12 aryl, C7-13 arylalkyl, or C7-13 alkylaryl and c is 0-1 and wherein the composition comprises less than or equal to about 2 wt % contaminants; wherein the contaminants comprise one or more of glycerol, acid, ethyl levulinate, water, or a high molecular weight byproduct having molecular weights that are at least 1.1 times greater than the molecular weight of the ketal adduct.

The above-described and other embodiments are further described in the drawings and detailed description that follow.

BRIEF DESCRIPTION OF THE DRAWINGS

The following figures are representative embodiments, wherein the like elements are numbered alike.

DETAILED DESCRIPTION

Figure 1:
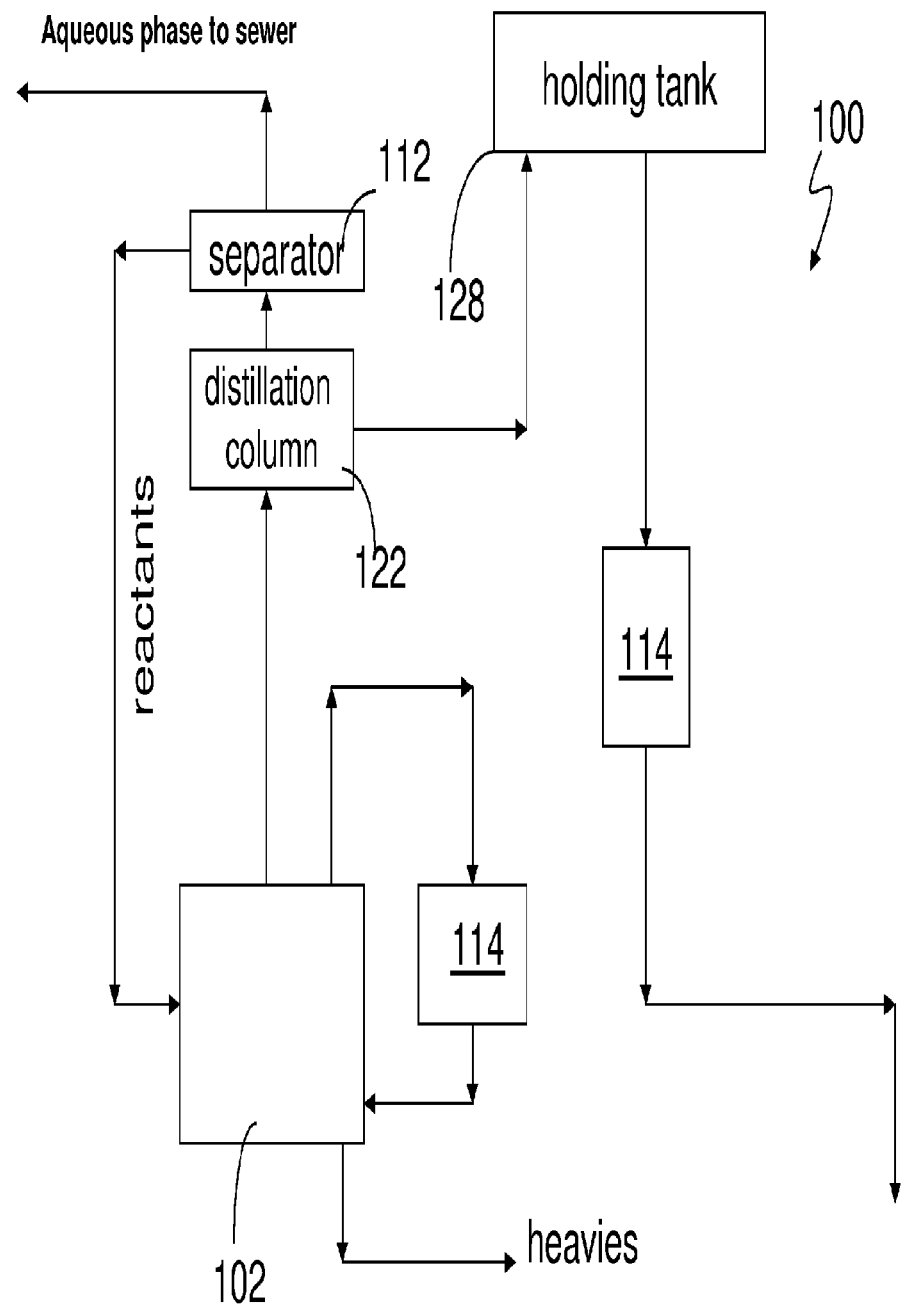
FIG. 1 is a schematic of an exemplary process used to produce acetals or ketals.

The inventors hereof have discovered improved methods for the selective, acid-catalyzed reaction of semialdehydes and ketoacids with alcohols, specifically polyols to produce acetals and ketals. These methods produce purer materials that exhibit improved stability without sacrificing yields.

Disclosed herein is a process for manufacturing ketals and acetals that have improved thermal stability, low color, high color retention or stability, and improved hydrolytic and shelf stability. The process involves reacting semialdehydes, ketoacids or esters thereof with alcohols, preferably polyols in a multistage process that involves recycling semialdehydes, ketoacids or esters and polyol, while removing acid catalyst and byproducts having a higher molecular weight condensation products from the process.

In an exemplary embodiment, the process involves acid catalyzing a reaction between an excess of ethyl levulinate with either glycerol or propylene glycol in a single or a multistage reactor under effective reaction conditions to produce a reaction product that comprises a glycerol ketal of ethyl levulinate or a propylene glycol ketal of ethyl levulinate respectively.

The reaction product comprises the respective ketal of ethyl levulinate as well as ethyl levulinate, and polyol, acid catalyst and higher molecular weight condensation products. In an exemplary embodiment, the vaporization of the excess ethyl levulinate is performed in a reaction section or in a fractionation section of the process set-up. The process set-up is detailed in the FIGS. 1, 2 and 3, which are detailed below. More than 99 wt % of the unreacted ethyl levulinate and polyol is removed from the reaction product by fractionation. The product is then subjected to distillation to produce a glycerol ketal of ethyl levulinate composition or a propylene glycol ketal of ethyl levulinate composition that contains less than 2 wt % of contaminants.

Contaminants include the reactants themselves, the acid catalyst, sulfur-containing species, byproducts such as water and/or alcohol, and high molecular weight species (sometimes referred to as "heavies" and include dimers, trimers, tetramers or oligomers). Contaminants also include carboxylic acid-type species, for example, the glycerol or propylene glycol ketal of levulinic acid, levulinic acid, acetic acid, formic acid, succinic acid, or any other base-titratable acid species.

The glycerol ketal of ethyl levulinate composition or the propylene glycol ketal of ethyl levulinate composition is substantially pure and displays improved chemical stability over time, low color, improved color stability over time, and improved hydrolytic stability over compositions that contain impurity levels greater than 2 wt % contaminants, such as those contaminants listed above.

In one embodiment, the glycerol ketal of ethyl levulinate composition or the propylene glycol ketal of ethyl levulinate composition contains less than 1 wt % contaminants and displays improved chemical stability over time, low color, improved color stability over time, and improved hydrolytic stability over compositions that contain impurity levels greater than 1 wt %.

In one embodiment, the glycerol ketal of ethyl levulinate composition or the propylene glycol ketal of ethyl levulinate composition contains less than 0.5 wt % contaminants and displays improved chemical stability over time, low color, improved color stability over time, and improved hydrolytic stability over compositions that contain impurity levels greater than 0.5 wt %.

Also disclosed herein is a glycerol ketal of ethyl levulinate composition that advantageously contains less than 1000 ppm water, less than 10 ppm acid, less than or equal to about 10,000 ppm of glycerol, less than or equal to about 0.5 wt % of dimers obtained from a reaction between monomers of the glycerol ketal of ethyl levulinate, less than or equal to about 0.5 wt % of aldol condensation products obtained from a reaction between the glycerol ketal of ethyl levulinate and ethyl levulinate, less than or equal to about 0.25 wt % of dimers obtained from a reaction between the glycerol ketal of ethyl levulinate and ethyl levulinate, less than or equal to about 0.1 wt % trimers obtained from an aldol condensation between the glycerol ketal of ethyl levulinate and the dimer product of ethyl levulinate and the glycerol ketal of ethyl levulinate and less than or equal to about 0.10 wt % trimers obtained from a reaction between the dimer of glycerol ketal of ethyl levulinate and ethyl levulinate. The low level of impurities permits the glycerol ketal of ethyl levulinate composition to have an extended shelf life during which it displays chemical stability over time, low color, color stability over time, and improved hydrolytic stability.

It is desirable for the glycerol ketal of ethyl levulinate composition to have an acid number (for total acid) of less than or equal to about 0.3, specifically less than or equal to about 0.2, specifically less than or equal to about 0.1, and more specifically less than or equal to about 0.05 when measured as per ASTM D 664. The acid number as determined by ASTM D 664 is given by the milligrams (mg) of potassium hydroxide (KOH) per gram of sample.

Examples of acids are strong acid or carboxylic acids, such as the glycerol ketal of levulinic acid, formic acid, acetic acid, levulinic acid, and propylene glycol ketal of levulinic acid.

Also disclosed herein is a propylene glycol ketal of ethyl levulinate composition that advantageously contains less than 1000 ppm water, less than 10 ppm acid, less than or equal to about 10,000 ppm of propylene glycol, less than or equal to about 0.5 wt % of dimers obtained from a reaction between the propylene glycol ketal of ethyl levulinate and propylene glycol, less than or equal to about 0.25 wt % of aldol dimers obtained from a reaction between the propylene glycol ketal of ethyl levulinate and ethyl levulinate, and less than or equal to about 0.25 wt % of dimers obtained from a reaction between 2 moles of the propylene glycol ketal of ethyl levulinate and 1 mole of propylene glycol. The low level of impurities permits the propylene glycol ketal of ethyl levulinate composition to have an extended shelf life during which it displays chemical stability over time, low color, color stability over time, and improved hydrolytic stability.

It is desirable for the propylene glycol ketal of ethyl levulinate composition to have an acid number (for total acid) of less than or equal to about 0.3, specifically less than or equal to about 0.2, specifically less than or equal to about 0.1, and more specifically less than or equal to about 0.05 when measured as per ASTM D 664. The acid number as determined by ASTM D 664 is given by the milligrams (mg) of potassium hydroxide (KOH) per gram of sample. Examples of acids are listed above.

As stated above, a semialdehyde or ketoacid is reacted with an alcohol, in particular a polyol, to produce an acetal or ketal. The semialdehyde or ketoacid is of formula (1):

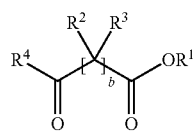
(1)

wherein each $R^1$, $R^2$, $R^3$, and $R^4$ is independently hydrogen, a C1-18 alkyl, a C3-10 cycloalkyl, a C1-18 alkenyl, a C6-18 aryl, a C7-19 arylalkyl, or a C7-19 alkylaryl, and b is 0-6.

In an embodiment, each $R^1$, $R^2$, $R^3$, and $R^4$ is independently a hydrogen, C1-12 alkyl, C3-6 cycloalkyl, C1-12 alkenyl, C6-12 aryl, C7-13 arylalkyl, or C7-13 alkylaryl, and b is 1-4. More specifically, each $R^1$ $R^2$, $R^3$, and $R^4$ is independently a hydrogen, C1-6 alkyl, C1-6 alkenyl, C6-12 aryl, C7-10 arylalkyl, or C7-10 alkylaryl and b is 0-6. Still more specifically, $R^1$ is a hydrogen, C1-6 alkyl, C1-6 alkenyl, C6-12 aryl, C7-10 arylalkyl, or C7-10 alkylaryl, each $R^2$ and $R^3$ is independently a hydrogen or C1-3 alkyl, $R^4$ is a C1-6 alkyl, C1-6 alkenyl, C6-12 aryl, C7-10 arylalkyl, or C7-10 alkylaryl, and b is 0-4. Even more specifically, $R^1$ is a hydrogen or C1-6 alkyl, each $R^2$ and $R^3$ is independently a hydrogen or C1-3 alkyl, $R^4$ is a C1-3 alkyl, and b is 0-3.

Semialdehydes of formula (1) have an aldehyde group (wherein $R^4$ is hydrogen) and a carboxylic acid group; specific examples of semialdehydes include 4-oxobutanoic acid, 5-oxopentanoic acid, 6-oxohexanoic acid, 7-oxoheptanoic acid, 3-oxopropanoic acid, 2-methyl-3-oxopropanoic acid, succinic semialdehyde, and adipic semialdehyde. Specific ester groups ($R^1$ in formula (1)) include methyl, ethyl, propyl, butyl, pentyl, and hexyl.

Ketoacids of formula (1) have a ketone group (wherein $R^4$ is not hydrogen) and a carboxylic acid group; specific ketoacids include pyruvic acid, acetoacetic acid, levulinic acid, 4-ketobutanoic acid, 5-ketohexanoic acid, 3-ketoadipic acid, 4-acetylbutyric acid, 2-phenylpyruvic acid, 2-keto-3-phenylpropanoic acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, 4-ketostearic acid, 9-ketopalmitic acid, 4-ketoheptanedioic acid, 2-oxo-3-butynoate, 2-ketoadipic acid, 3-keto-adipic acid, and the esters thereof. Specific ester group ($R^1$ in formula (1)) include methyl, ethyl, propyl, butyl, pentyl, and hexyl.

In a specific embodiment, the semialdehyde or ketoacid of formula (1) is levulinic acid (4-oxopentanoic acid) or an ester thereof, wherein $R^1$ is hydrogen or a C1-6 alkyl, $R^2$ and $R^3$ are each hydrogen, $R^4$ is methyl, and b is 2. In an exemplary embodiment, the semialdehyde or ketoacid of formula (1) is ethyl levulinate.

The alcohol can be an alcohol of formula (2) a polyol of formula (3), or a polymeric polyol of formula (4):

(2)

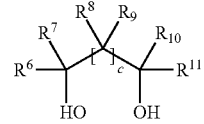
(3)

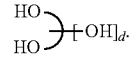
(4)

In formula (2), $R^5$ is a C1-12 alkyl, C3-6 cycloalkyl, C2-12 alkenyl, C2-12 alkynyl, C6-12 aryl, C7-13 arylalkyl, or C7-13 alkylaryl, each of which can optionally be substituted with one or more addition hydroxyl groups. In a specific embodiment, $R^5$ is a C1-6 alkyl, C1-6 alkenyl, C6-12 aryl, C7-10 arylalkyl, or C7-10 alkylaryl. Still more specifically, $R^5$ is a C1-3 alkyl. Specific examples of monols of formula (2) include methanol, ethanol, 1-propanol, 2-propanol, 1-butanol, 1-pentanol, 1-hexanol, cyclohexanol, ethynyl alcohol, 3-methylpent-1-yn-3-ol, tetradec-9-ynol, phenol, benzyl alcohol, toluol, and xylyl alcohol.

As stated above, $R^5$ can optionally be substituted with one or more hydroxyl groups. In these compounds, the alcohol does not form a cyclic ketal with the semialdehydes, ketoacids, semialdehydes, or esters thereof. Such polyols react as monofunctional alcohols such that two moles of the compound react to produce acetal or ketal group. Specific examples of compounds of formula (2) that do not form cyclic ketals or acetals include 1,4-butenediol, diethylene glycol (($HOCH_2CH_2)_2O$), xylene glycol, 2-butyne-1,4-diol, 3-hexyne-3,5-diol (SURFYNOL® 82, available from Air Products of Allentown, Pa.) and other alkyne-based polyol products marketed under the SURFYNOL® brand name by Air Products of Allentown, Pa.

In the polyol of formula (3) at least two alcohol groups are present, and each $R^6$, $R^7$, $R^{10}$, and $R^{11}$ is independently a hydrogen, C1-12 alkyl, C1-12 hydroxyalkylene, C1-12 alkyl substituted with up to six hydroxy groups, C3-6 cycloalkyl, C2-5 heterocycloalkyl, C1-12 alkenyl, C1-12 hydroxyalkenyl, C6-12 aryl, C7-13 arylalkyl, or C7-13 alkylaryl, each $R^8$ and $R^9$ is independently a hydrogen, hydroxyl, C1-12 alkyl, C1-12 hydroxyalkyl, C3-6 cycloalkyl, C1-12 alkenyl, C1-12 hydroxyalkenylene, C6-12 aryl, C7-13 arylalkyl, or C7-13 alkylaryl and c is 0-1. In a specific embodiment, each $R^6$, $R^7$, $R^{10}$, and $R^{11}$ is independently a hydrogen, C1-6 alkyl, C1-6 hydroxyalkylene, C1-6 alkenyl, C6-12 aryl, C7-10 arylalkyl, or C7-10 alkylaryl, each $R^8$ and $R^9$ is independently a hydrogen, hydroxyl, C1-6 alkyl, C1-6 hydroxyalkylene, C1-6 alkenyl, C6-12 aryl, C7-10 arylalkyl, or C7-10 alkylaryl and c is 0-1. Still more specifically, each $R^6$, $R^7$, $R^{10}$, and $R^{11}$ is independently a hydrogen, C1-3 alkyl, or C1-3 hydroxyalkylene, each $R^8$ and $R^9$ is independently a hydrogen, C1-4 alkyl, or C1-3 hydroxyalkylalkylene, and c is 0-1.

Specific examples of polyols of formula (3) include 1,2-ethanediol (ethylene glycol), 1,2-propanediol (propylene glycol), 1,3-propanediol, 1,2,3-propanetriol (glycerol), diglycerol (a mixture of glycerol dimers coupled at primary and secondary hydroxyl groups), 2,2-dimethyl-1,3-propanediol (neopentyl glycol), 1,1,1-trimethylolpropane, 1,2-butanediol, 1,3-butanediol, pentaerythritol, cyclohexane-1,2-diol, 1,4-dioxane-2,3-diol, 1,2,3-butanetriol, 1,3,4-butanetriol, 1,2,3-heptanetriol, 4-menthane-1,7,8-triol, 3-butene-1,2-diol, indane-1,2-diol, and pentose and hexose sugar alcohols including mannitol, sorbitol, xylitol, threitol, erythrol, erythritol, maltitol, lactitol, raffinose, and stachyose; pentaerythritol derivatives and other polyhydric alcohol derivatives such those sold under the trade name CHARMOR® by Perstorp Polyols, Inc. of Toledo, Ohio.

In a specific embodiment of the polyol of formula (3), each $R^6$ and $R^7$ is hydrogen, $R^{10}$ is hydrogen, methyl, ethyl, or hydroxymethylene, and $R^{11}$ is a methyl, —$CH_2OH$, —$CH(OH)CH_2OH$, —$(CH(OH))_3CH_2OH$, and c is 0. In another specific embodiment of formula (3), each $R^6$, $R^7$, and $R^{10}$ is hydrogen, $R^{11}$ is methyl, —$CH_2OH$, —$CH(OH)CH_2OH$, or —$(CH(OH))_3CH_2OH$, and c is 0. Alternatively, each $R^6$ and $R^7$ is hydrogen, $R^{10}$ is methyl or ethyl, $R^{11}$ is $CH_2OH$, and c is 0.

In an exemplary embodiment, the polyol of formula (3) is propylene glycol, while in another embodiment, the polyol of formula (3) is glycerol.

In the polymeric polyols of formula (4), d is 0-500, specifically 0-250, more specifically 0-100, still more specifically 10-50 or 0-10. The polymeric polyols have repeating units, for example from 3 to 1,000 repeating units wherein all or a portion of the units can include a hydroxyl group. In some embodiments, the hydroxyl groups are only present as terminal groups. Such polymeric polyols include polyvinyl alcohol and copolymers thereof, polyether polyols based on ethylene glycol, such as CARBOWAX® polyethylene glycols, available from Dow® Company of Midland, Mich.; polyether diols and polyols based on propylene glycol or combinations of ethylene glycol and propylene glycol, such as those sold by the Dow® Company of Midland, Mich., and polyether glycols such as those produced by the INVISTAT™ Company of Wichita, Kans. under the trade name TERETHANE®; dendritic polyols, for example those sold under the trade name BOLTORN® by Perstorp Polyols, Inc. of Toledo, Ohio; polycarbonatediols of varying molecular weights, such as L467m, L600m, and L565m, available from Asahi Kasei Corporation (Tokyo, Japan); polyols based on hydroxylated vegetable oils, such as those sold under the trade name BiOH®, available from the Cargill Company of Wayzata, Minn.; hydroxyl-terminated polybutadienes, such as HTPB R45M, sold by Aerocon Systems of San Jose, Calif.; the polyols include produced by the Everchem Company of Media, Pa., or the Maskimi Polyol Sdn. Bhd. of Kajang, Selango Darul Ehsan, Malaysia and the polyols used in the Union Carbide Company (South Charleston, W. Va.) publication by Carey, M. A. et al., "Rapid Method for Measuring the Hydroxyl Content of Polyurethane Polyols" (published on the internet at http://www.polyurethane.org/s api/doc_paper.asp7CID=1044&D1D~4060).

Acetalization with a monol of formula (2) or a polyol of formula (3) yields the acetal adduct of formula (5) or the ketal adduct of formula (6), respectively:

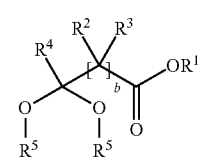

(5)

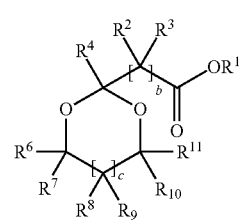

(6)

wherein each of $R^1$, $R^2$, $R^3$, $R^4$, $R^5$, $R^6$, $R^7$, $R^8$, $R^9$, $R^{10}$, $R^{11}$, b, and c are as defined above.

In a specific embodiment, in the acetal of formula (5), $R^1$ is a hydrogen, C1-6 alkyl, C1-6 alkenyl, C6-12 aryl, C7-10 arylalkyl, or C7-10 alkylaryl, each $R^2$ and $R^3$ is independently hydrogen or C1-3 alkyl, $R^4$ is hydrogen, b is 1-4, each $R^5$ and R is independently methyl, ethyl, or —$CH_2OH$.

In a specific embodiment, in the ketal of formula (6), $R^1$ is a hydrogen, C1-6 alkyl, C1-6 alkenyl, C6-12 aryl, C7-10 arylalkyl, or C7-10 alkylaryl, each $R^2$ and $R^3$ is independently hydrogen or C1-3 alkyl, $R^4$ is C1-6 alkyl, C1-6 alkenyl, C6-12 aryl, C7-10 arylalkyl, or C7-10 alkylaryl, and b is 1-4, each $R^6$ and $R^7$ is hydrogen, $R^{10}$ is hydrogen, methyl, ethyl, or hydroxymethylene, and $R^{11}$ is a methyl, —$CH_2OH$, —$CH(OH)CH_2OH$, —$(CH(OH))_3CH_2OH$, and c is 0.

In another specific embodiment of formula (6), $R^1$ is a hydrogen or C1-3 alkyl, each $R^2$ and $R^3$ is independently a hydrogen or C1-3 alkyl, $R^4$ is a C1-3 alkyl, and b is 1-3. $R^6$, $R^7$, and $R^{10}$ is hydrogen, $R^{11}$ is methyl, —CH$_2$OH, —CH(OH)CH$_2$OH, or —(CH(OH))$_3$CH$_2$OH, and c is 0; or, alternatively, each $R^6$ and $R^7$ is hydrogen, $R^{10}$ is methyl or ethyl, $R^{11}$ is CH$_2$OH, and c is 0.

Still more specifically, the ketal adduct of formula (6) is the propylene glycol adduct of a levulinic acid ester, having formula (6a), or the 1,2-propanediol adduct of a levulinic acid ester, having formula (6b):

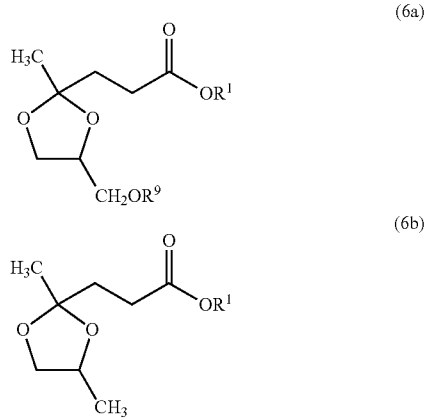

wherein each $R^1$ is as defined above, specifically a C1-6 alkyl, more specifically ethyl or butyl. Formula 6(a) wherein $R^1$ is ethyl and $R^9$ is hydrogen is the glycerol ketal of ethyl levulinate and formula 6(b) wherein $R^1$ is ethyl is the propylene glycol ketal of ethyl levulinate.

Reaction of the semialdehyde or ketoacid of formula (1) with the polymeric polyol of formula (4) also yields an acetal or ketal adduct, respectively. In the case of polymeric polyols of formula (4) not configured with one or more pairs of hydroxyls in the 1,2 or 1,3 position on a polymer chain, it is statistically possible to form a cyclic ketal by an intramolecular reaction of two hydroxyl groups present on the polymeric polyol with a ketoacid, semialdehyde, or an ester thereof. However, the main product of such reactions is not, in embodiments, the result of such an intramolecular reaction of the polyol.

In one embodiment, in order to manufacture the ketal or acetal, the semialdehydes, ketoacids or esters thereof are present in the reaction mixture preferably in an excess when compared with the alcohol. The presence of excess semialdehydes, ketoacids or esters thereof drives the conversion to ketals or acetals. In one embodiment, the molar ratio of the semialdehydes, ketoacids or esters to the alcohols is greater than or equal to about 1.5:1, specifically greater than or equal to about 2:1, more specifically greater than or equal to about 3:1 and more specifically greater than or equal to about 5:1. In one embodiment, the molar ratio of the semialdehydes, ketoacids or esters to the alcohols is less than or equal to about 1:2, specifically less than or equal to about 1:3, and more specifically less than or equal to about 1:5. While the excess semialdehydes, ketoacids or esters thereof drive conversion, the semialdehydes, ketoacids or esters are also contaminants and need to be removed from the product. In one embodiment, when ethyl levulinate is reacted with glycerol, the ethyl levulinate is added in a stoichiometric excess when compared with the glycerol. In another embodiment, when ethyl levulinate is reacted with propylene glycol, the ethyl levulinate is added in a stoichiometric excess when compared with the propylene glycol.

The acetalization or ketalization is conducted in the presence of an acid catalyst, which can be either a Lewis or Brønsted-Lowry acid. Acid catalysts that are known homogeneous catalysts for either acetal or ketal formation or esterification or transesterification reactions can be used, for example strong protic acid catalysts, e.g., Brønsted-Lowry acids that have a Ka of 55 or greater. Examples of strong protic acid catalysts include sulfuric acid, arylsulfonic acids and hydrates thereof such as p-toluenesulfonic acid monohydrate, methane sulfonic acid, camphor sulfonic acid, dodecyl benzene sulfonic acid, perchloric acid, hydrobromic acid, and hydrochloric acid. In other embodiments, weak protic acid catalysts, e.g., having a Ka of less than 55, can be used, for example phosphoric acid, orthophosphoric acid, polyphosphoric acid, and sulfamic acid. Aprotic (Lewis acid) catalysts can include, for example, titanium tetrachloride, aluminum trichloride, and boron trifluoride. A combination comprising any one or more of the foregoing acid catalysts can be used. In some embodiments, the method employs a substantially nonvolatile acid catalyst such that the acid does not transfer into the distillate, such as sulfuric or sulfamic acid. In an exemplary embodiment, the homogenous catalyst is camphor sulfonic acid.

Instead of, or in addition to the homogenous acid catalyst, a heterogenous acid catalyst can be used, where the acid catalyst is incorporated into, onto, or covalently bound to, a solid support material such as resin beads, membranes, porous carbon particles, zeolite materials, and other solid supports. Many commercially available resin-based acid catalysts are sold as ion exchange resins. One type of useful ion exchange resin is a sulfonated polystyrene/divinyl benzene resin, which supplies active sulfonic acid groups. Other commercial ion exchange resins include LEWATIT® ion exchange resins sold by the Lanxess Company of Pittsburgh, Pa.; DOWEX™ ion exchange resins sold by the Dow Company of Midland, Mich.; and AMBERLITE® and AMBERLYST® ion exchange resins sold by the Rohm and Haas Company of Philadelphia, Pa. In embodiments, AMBERLYST® 15, Nafion® NR 50 and SAC® 13 resins may also be used as heterogeneous catalysts. In these embodiments, the resin based catalyst is washed with water, and subsequently, an alcohol, such as methanol or ethanol, and then dried prior to use. Alternatively, the resin is not washed before its first use. In use, the heterogeneous catalysts are added to a reaction mixture, thereby providing a nonvolatile source of acid protons for catalyzing the reactions. The heterogenous catalysts can be packed into columns or beds and the reactions carried out therein. As the reagents elute through the column, the reaction is catalyzed and the eluted products are free of acid. In other embodiments, the heterogenous catalyst is slurried in a pot containing the reagents, the reaction is carried out, and the resulting reaction products filtered or distilled directly from the resin, leaving an acid-free material.

The amount of acid catalyst is about 2 to 10,000 parts per million (ppm), specifically about 10 to about 5,000 ppm, specifically about 15 to about 1000 ppm, and more specifically about 20 to about 600 ppm, relative to the total weight of the reactants. In this case, the reactants are the sum of the polyol of formula (3), and the semialdehyde, ketoacid, or ester thereof of formula (1).

When camphor sulfonic acid is used as the acid catalyst to produce the ketal or acetal, it is used in amounts of about 5 to 5,000 parts per million (ppm), specifically about 10 to about 1,000 ppm, specifically about 15 to about 800 ppm, and more specifically about 20 to about 500 ppm, relative to the total weight of the reactants. In this case, the reactants are the sum of the polyol of formula (3), and the semialdehyde, ketoacid, or ester thereof of formula (1). It is to be noted various isomers of camphor sulfonic acid may be used to catalyze the reaction and that racemic mixtures of the various isomers of camphor sulfonic acid may be used to catalyze the reaction.

The acid catalyst may be charged directly into the reactant mixture comprising the semialdehyde, ketoacid, or ester thereof and the alcohol or alternatively it may be diluted in water or one of the reactants prior to being charged into the reactant mixture. The acid catalyst may be diluted to about 0.01N to about 5.0N, specifically about 0.1N to about 4N, and more specifically about 0.5N to about 3N prior to introduction into the reactant mixture. The dilute acid catalyst may be continuously added to the reactant mixture throughout the course of the reaction or alternatively it may be added instantaneously to the reactant mixture in a single pass.

In one embodiment, in one method of manufacturing the ketal or acetal, the semialdehyde, ketoacid, or keto ester and the alcohol (also known as the "reactants") are charged to a reactor along with the catalyst. The reaction to produce the ketal or acetal may be conducted in either a batch reactor, a continuous reactor or in a semicontinuous reactor. It is desirable for the reactor to have heating, cooling, agitation, condensation, vacuum, and distillation facilities.

In a batch reactor, the reactants and catalyst are charged to the reactor in batches and the produce is extracted from the reactor in batches only after the reaction has been completed to an extent of greater than 80%. While a batch reactor may be used, it is desirable to use a batch reactor when the product is manufactured by introducing the dilute acid catalyst into the reactor in one charge. An exemplary batch reactor is a stainless steel, glass-lined, or Hastelloy-type reactor. An example of a batch reactor is a continuous stirred tank reactor. Another example of a reactor is a reactor with a recirculation loop. It is desirable for the batch reactor to be equipped with distillation facilities for further purification of the product.

FIG. 1 is a depiction of an exemplary batch reactor system 100. With reference now to the FIG. 1, an exemplary system 100 for manufacturing the ketal or acetal comprises a first reactor 102 in fluid communication with an optional condenser 122, a separator 112, a packed column or bed 114, and a holding tank 128.

In one embodiment, in one method of manufacturing the acetal or ketal in the batch reactor system 100, the reactants are charged to the first reactor 102. In the reactor 102, glycerol or propylene glycol is contacted with ethyl levulinate and an acid catalyst in a reactor under reaction conditions effective to produce a product that comprises a glycerol ketal of ethyl levulinate or propylene glycol ketal of ethyl levulinate, while removing water as a by-product. The product comprising the glycerol ketal of ethyl levulinate or propylene glycol ketal of ethyl levulinate is subjected to distillation in the distillation column 122 under effective distillation conditions to produce a resulting product that comprises either the glycerol ketal of ethyl levulinate or the propylene glycol ketal of ethyl levulinate and less than or equal to about 2 wt % contaminants; wherein the contaminants comprise one or more of glycerol, acid species, ethyl levulinate, water, or a high molecular weight byproduct having molecular weights that are at least 1.5 times greater than the molecular weight of the glycerol ketal of ethyl levulinate.

The resulting reaction product may optionally be fractionated in a distillation column (not shown) under fractionation conditions to separate fractionated materials (light materials) from the product (heavy materials) until the product comprises less than 1000 parts per million of glycerol, ethyl levulinate, or propylene glycol. The light materials comprise the reactants and reaction products that have vapor pressures lower than the product. The heavy materials comprise the reactants and reaction products that have vapor pressures greater than or equal to the product.

When the glycerol ketal of ethyl levulinate is being manufactured the reaction product after fractionation, comprises less than 1000 parts per million of glycerol, while if the propylene glycol ketal of ethyl levulinate is being manufactured, the product comprises less than 1000 parts per million of ethyl levulinate.

In one embodiment, the product is passed to a holding tank 128 and then optionally through a bed 114 disposed downstream of the holding tank 128. The bed is generally a packed bed that comprises inorganic salts, bases, molecular sieves or buffers that can remove acid species and catalyst impurities from the product. This packed bed can be before or after the distillation.

The product comprising the glycerol ketal of ethyl levulinate comprises less than or equal to about 2 wt % contaminants; wherein the contaminants comprise one or more of glycerol, acid species, ethyl levulinate, water, or a high molecular weight byproduct having molecular weights that are at least 1.5 times greater than the molecular weight of the glycerol ketal of ethyl levulinate. The product comprising the or propylene glycol ketal of ethyl levulinate comprises less than or equal to about 2 wt % contaminants; wherein the contaminants comprise one or more of glycerol, acid species, ethyl levulinate, water, or a high molecular weight byproduct having molecular weights that are at least 1.1 times greater than the molecular weight of the glycerol ketal of ethyl levulinate.

Figure 2:
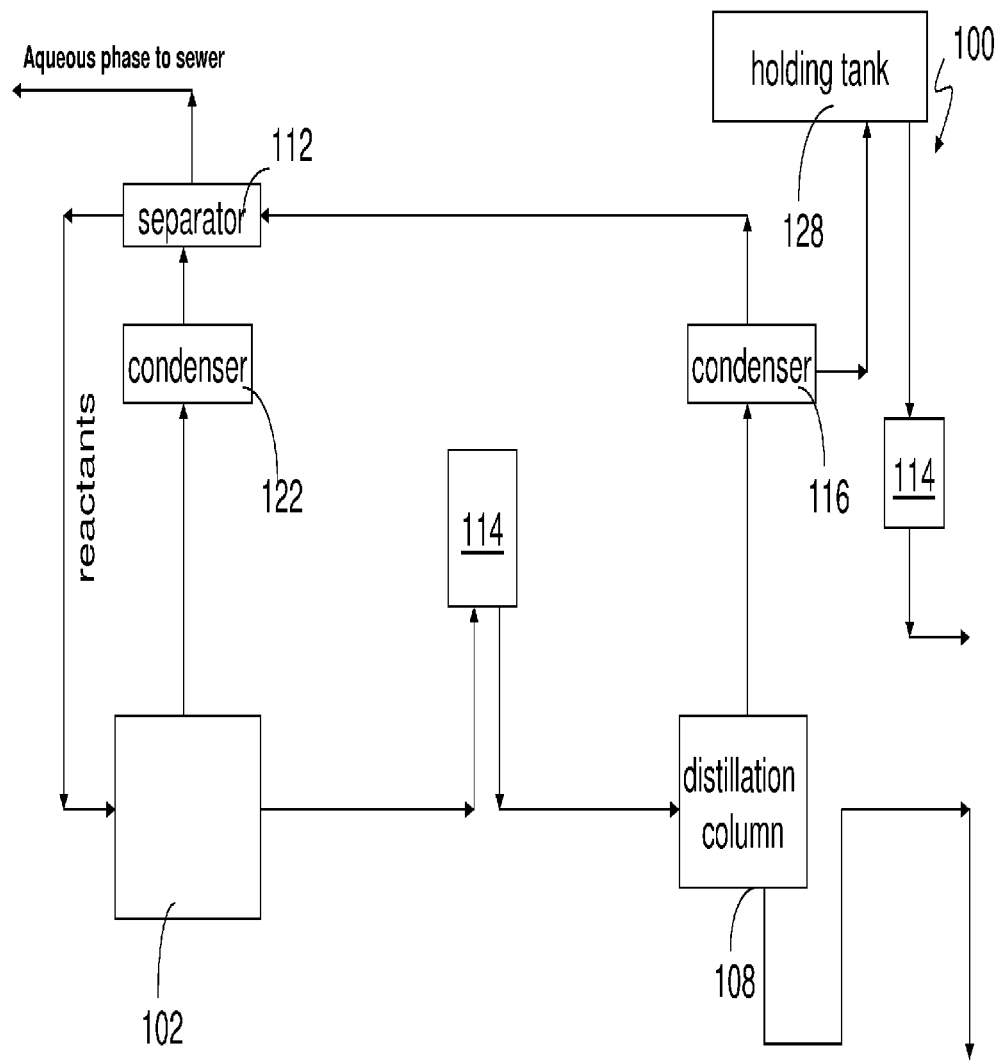
FIG. 2 is another schematic of an exemplary process used to produce acetals or ketals.

The FIG. 2 is another depiction of an exemplary batch reactor system 100. With reference now to the FIG. 2, an exemplary system 100 for manufacturing the ketal or acetal comprises a first reactor 102 in fluid communication with a first distillation column 108, a separator 112, a (filtration) bed 114, a first condenser 116 and a holding tank 128. The first reactor 102 is fitted with an optional condenser 122, while the first distillation column 108 is fitted with a first condenser 116.

In one embodiment, in one method of manufacturing the acetal or ketal in the batch reactor system 100, the reactants are charged to the first reactor 102. In the first reactor 102, glycerol or propylene glycol is contacted with ethyl levulinate and an acid catalyst in a reactor under reaction conditions effective to produce a product that comprises a glycerol ketal of ethyl levulinate or propylene glycol ketal of ethyl levulinate while removing the by-product, water. The resulting reaction product is then fractionated in a distillation column (108) under fractionation conditions to separate fractionated materials from the product until the product comprises less than 1000 parts per million of glycerol, ethyl levulinate, or propylene glycol. Fractionated materials comprising ethyl levulinate, polyol, and other distilled compounds and impurities are recycled back to the reactor. The product comprising the glycerol ketal of ethyl levulinate are then subjected to distillation in the distillation column 108 under effective distillation conditions to produce a resulting product that comprises the glycerol ketal of ethyl levulinate and less than or equal to about 2 wt % contaminants; wherein the contaminants comprise one or more of glycerol, acid, ethyl levulinate, water, or a high molecular weight byproduct having molecular weights that are at least 1.5 times greater than the molecular weight of the glycerol ketal of ethyl levulinate.

The product comprising the propylene glycol ketal of ethyl are then subjected to distillation in the distillation column 108 under effective distillation conditions to produce a resulting product that comprises the propylene glycol ketal of ethyl levulinate and less than or equal to about 2 wt % contaminants; wherein the contaminants comprise one or more of glycerol, acid, ethyl levulinate, water, or a high molecular weight byproduct having molecular weights that are at least 1.1 times greater than the molecular weight of the propylene glycol ketal of ethyl levulinate.

In one embodiment, the product is passed through a bed 114 disposed downstream of the reactor 102 and upstream of the distillation column 108. The bed is generally a packed bed that comprises inorganic salts, bases, molecular sieves or buffers that can remove acid species from the product.

As can be seen in the FIG. 2, the first distillation column 108 is fitted with a condenser 116. The first reactor 102 also has a condenser 120 in which water, polyol and ethyl levulinate vapors are condensed. The vapors from the condenser 120 are then discharged to a separator 112 to separate an organic phase that comprises primarily reactants (e.g., semialdehyde, ketoacid, or the ester thereof) from byproducts (e.g., water). The reactants are generally recycled to the first reactor 102, while the byproducts are extracted and removed from the manufacturing process. In one embodiment, distillation, molecular sieves, superabsorbents, or some other means for removal of water from the reaction mixture may optionally be used in the process.

Vapors from the first condenser 116 are also discharged to the separator 112 to separate an organic phase that comprises primarily reactants (e.g., semialdehyde, ketoacid, or the ester thereof) from byproducts (e.g., water). In one embodiment, the bottom of the distillation column can be purged to remove the "heavy species" (e.g., high molecular weight species, dark-colored species, and unwanted acid catalyst, carboxylic acid components and catalyst by-products). The resulting purified acetal or ketals are removed to the holding tank 128.

In a continuous reactor system, the reactants are charged to a first reactor, conversion of reactants to products is measured to be greater than or equal to about 50%, and a portion of the product mixture from the first reactor is subjected to additional finishing processes in a second reactor, while at the same time additional reactants and catalyst are continuously being charged to the first reactor to be converted into ketals or acetals. A continuous reactor system generally employs a plurality of reactors in series or parallel so that various parts of the process can be conducted in different reactors simultaneously.

In one embodiment, the reactor comprises a plurality of reactors (e.g., a multistage reactor system) that are in fluid communication with one another in series or in parallel. The plurality of reactors are used to react the semialdehyde, ketoacid, or ester thereof with the alcohol, to recycle the reactants and to remove unwanted byproducts and impurities so as to obtain a ketal or an acetal that is stable and has a long shelf life. In one embodiment, a portion of the plurality of reactors may be used primarily to react reactants to manufacture ketals or acetals, while another portion of the plurality of reactors may be used primarily to remove from the ketals or acetals excess reactants, residual catalyst and other byproducts that may hamper the formation of a stable product that has good shelf stability.

Figure 3:
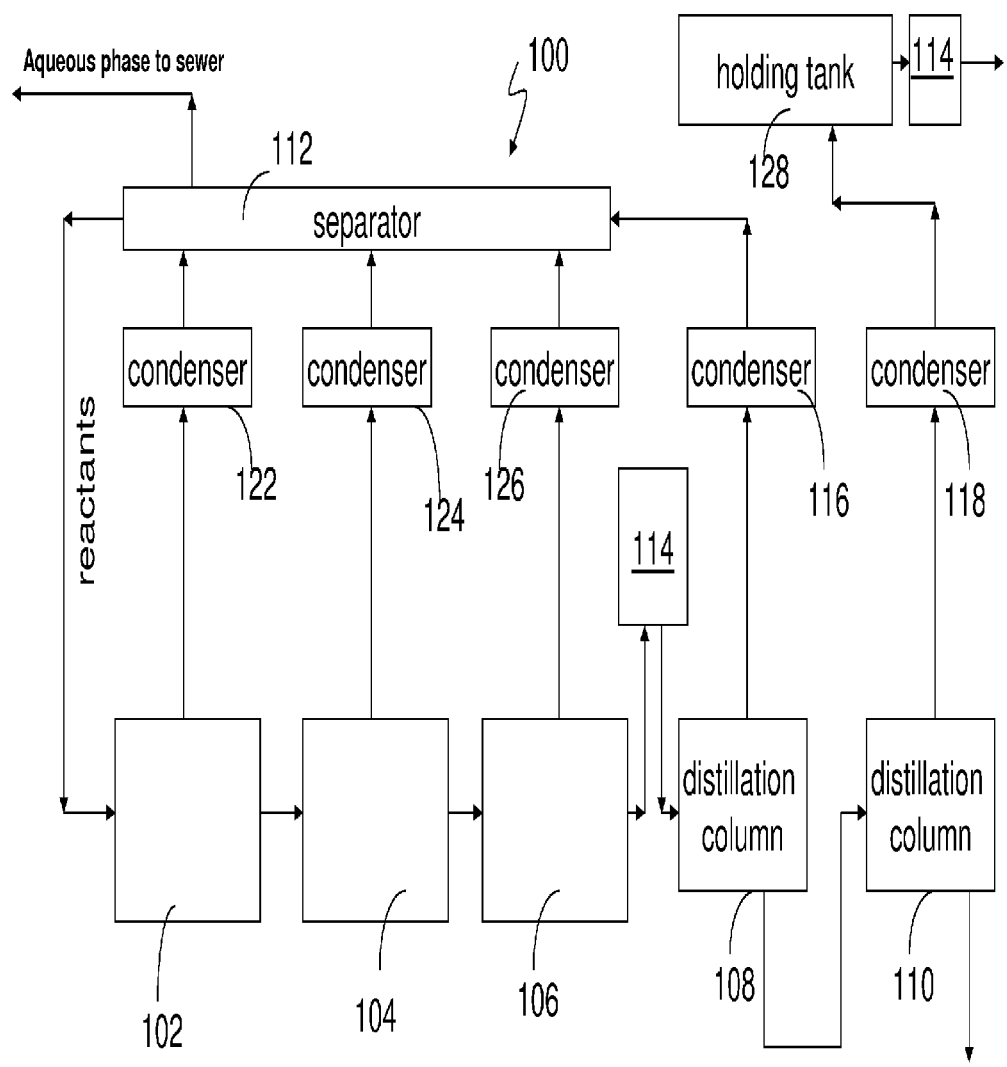
FIG. 3 is another schematic of another exemplary process used to produce acetals or ketals.

With reference now to FIG. 3, another exemplary system 100 for manufacturing the ketal or acetal comprises a plurality of reactors—a first reactor 102, a second reactor 104, a third reactor 106, a packed bed or packed column of inorganic material, a first distillation column 108 and a second distillation column 110 in fluid communication with one another. The first, second and third reactors are each fitted with condensers 122, 124 and 126 respectively. The first distillation column 108 and the second distillation column 110 are also fitted with condensers 116 and 118 respectively.

While the third reactor in FIG. 3 is the final reactor, the final reactor could be the first reactor or the second reactor. Additionally, it could be a fourth, a fifth, or a sixth reactor if desired. In other words, the system may comprise as many reactors as desired to manufacture a product that is stable and has a long shelf life. In another embodiment, there may be more than two distillation columns. For example, the system 100 may use three, four or five distillation columns. Also, there may be more than one packed bed or column of inorganic material prior to distillation. The packed beds or columns may be used in series or parallel.

In other words, the system 100 can comprise "n" reactors that are in fluid communication with each other and that may be arranged in series or in parallel. In one embodiment, n is an integer from 1 to 20, specifically 2 to 10, and more specifically 3 to 6. In an exemplary embodiment, n is 3. The system can also comprise "m" distillation columns, where m can be an integer from 1 to 8, specifically 1 to 6, and more specifically about 2 to about 4. In an exemplary embodiment, the number of distillation columns is 2. One column will be used to remove excess ethyl-levulinate, polyol, and other distillable compounds and impurities while the other distillation column is used to purify the ketal product. The number of distillation columns used to purify the ketal may be 1 column, 2 columns or even 3 or more columns.

In one embodiment, the alcohol (e.g., glycerol or propylene glycol) is reacted with an ester of levulinic acid (e.g., ethyl levulinate) in the first reactor 102 with an acid catalyst to produce a glycerol ketal of ethyl levulinate product or a propylene glycol ketal of ethyl levulinate product. The by-product, water, is removed and condensed as the reaction proceeds. The glycerol ketal of ethyl levulinate product or a propylene glycol ketal of ethyl levulinate product are interchangeably referred to as a "product that comprises a glycerol ketal of ethyl levulinate" or as a "product that comprises a propylene glycol ketal of ethyl levulinate" respectively.

After reaction, the glycerol ketal of ethyl levulinate product or the propylene glycol ketal of ethyl levulinate product contains excess reactant (ethyl levulinate, glycerol or propylene glycol), acid catalyst, acid species, and high molecular weight species which need to be removed. The removal of the excess reactant, acid catalyst, acid species, and high molecular weight species is conducted in the first and second distillation columns to produce a glycerol ketal of ethyl levulinate composition or a propylene glycol ketal of ethyl levulinate composition that contains less than 2 wt % of the excess reactant, acid catalyst and high molecular weight species. In an exemplary embodiment, the glycerol ketal of ethyl levulinate composition or the propylene glycol ketal of ethyl levulinate composition contains less than 1 wt %, and more specifically, less than 0.5 wt % of the excess reactant, acid catalyst and high molecular weight species. When a glycerol ketal of ethyl levulinate composition or when a propylene glycol ketal of ethyl levulinate composition is to be produced, the ethyl levulinate is generally charged to the reactor in excess when compared with the glycerol or propylene glycol. The excess ethyl levulinate drives conversion but also acts as a reactant and it is therefore desirable to remove the excess ethyl levulinate after the first reactor 102, the second reactor 104 and the third reactor 106 and to resupply it to the first reactor 102. In an exemplary embodiment, the excess ethyl levulinate is removed after the third reactor 106 and recycled to the first reactor 102. The reactors function to drive the reaction between the glycerol or propylene glycol and the ethyl levulinate by removing water.

In one embodiment, one of the reactors in the system 100 to be a continuous stirred tank reactor. In an embodiment the system 100 comprises at least one distillation column that can facilitate the removal of unwanted byproducts of a high molecular weight (dimers, trimers, and larger units such as oligomers). Recirculation reactors may also be used that do not have an agitator.

As used herein, byproducts of a high molecular weight have molecular weights that are at least at least 1.1 times greater, specifically at least 1.5 times greater, specifically at least 1.8 times greater than the molecular weight of the desired acetal or ketal. For example, when the desired ketal is the glycerol ketal of ethyl levulinate, the high molecular weight byproducts include byproducts having a molecular weight that is at least 1.1, specifically at least 1.5, and more specifically at least 1.8 times greater than the molecular weight of the glycerol ketal of ethyl levulinate. Such byproducts include various dimers, trimers, and other larger oligomers. The dimers, trimers, and oligomers can be produced by a condensation reaction between two, three, or more molecules of the desired acetal or the ketal; a reaction between the semialdehyde, ketoacid, or ester, thereof and the desired acetal or ketal; a reaction between the semialdehyde, ketoacid, or ester thereof and an aldol of the desired acetal or ketal, or a reaction between the semialdehyde, ketoacid, or ester thereof, the aldol of the desired acetal or ketal, and the desired acetal or ketal.

In one embodiment, the system (not shown) for producing ketals or acetals may comprise a single continuous stirred tank reactor in fluid communication with a reboiler that is fitted with a distillation column (see FIG. 2). In another embodiment, the system (not shown) for producing ketals or acetals may comprise a single continuous stirred tank reactor that is fitted with a distillation column (see FIG. 1). The distillation column is used to remove excess reactants and to distill the final product by removing higher molecular weight species, acid species, and catalyst that are not desired in the acetal or ketal.

In an exemplary embodiment, it is desirable to use a plurality of reactors (e.g., a multi-stage reactor system) as shown in the system 100 of FIG. 3, to achieve conversion of the alcohol and the semialdehyde, ketoacid, or ester thereof to an acetal or ketal. A multi-stage reactor system is used to reduce the residence time of the reactants in the reactors. It also provides the ability to change temperature and pressure without causing spikes in temperature and pressure or unduly long heat-up and cool-down times that are produced in a system that comprises a single reactor and that are damaging to the quality of the acetal or ketal.

The residence time required for high conversion is reduced by utilizing a multiple stage reactor system. This improves product yield by reducing the formation of byproducts, due to relatively low residence times in each reactor. Additionally, since high conversion is highly dependent upon vapor-liquid equilibria, multiple stages allow for greater flexibility of temperature and pressure in a continuous process in order to maximize conversion and limit by-product formation. By operating reactors at different temperatures and pressures, including decreasing pressures as the reaction progresses, a conversion of greater than or equal to about 90%, specifically greater than or equal to about 95% of the reactants can be achieved.

With reference now again to FIG. 3, the reactants are generally introduced into the first reactor 102 along with the catalyst. A combination of the reactants, products and byproducts are transferred in sequence from the first reactor 102 to the second reactor 104, the third reactor 106, optionally, the packed bed of inorganic material (114), the first distillation column 108 and the second distillation column 110. In each stage, the manufacturing process is further completed by removing water, excess reactants and/or byproducts to obtain a stable ketal or acetal in the second distillation column 110.

In an exemplary embodiment, the first reactor 102 is a continuous stirred tank reactor into which the semialdehyde, ketoacid, or ester thereof and the alcohol are charged along with the acid catalyst. The first reactor 102 has a condenser 122 in which water and ethyl levulinate vapors are condensed. This is also known as the fractionation step in which the "light fractionated materials" comprising water, polyol, ethyl levulinate, impurities, and trace amounts of the ketals or acetals are separated from the "heavy fractionated materials" which include the product and other contaminants. A portion of the reactants and byproducts are condensed in the first condenser. The vapors from the first condenser are then discharged to a separator 112 to separate an organic phase that comprises primarily reactants (e.g., semialdehyde, ketoacid, or the ester thereof) from byproducts (e.g., water). The reactants are generally recycled to the first reactor 102, while the byproducts are extracted and removed from the manufacturing process. In one embodiment, molecular sieves, distillation, superabsorbents, or some other means for removal of water from the reaction mixture may optionally be used in the process.

The reaction can be carried out in the presence of an optional solvent that is substantially inert under reaction conditions, such as aliphatic or aromatic hydrocarbons, ethers or chlorinated hydrocarbons. Such solvents can also be used to remove water formed during the reaction by an azeotropic distillation. In one embodiment, toluene, benzene or another inert solvent could be used.

The reaction may be alternatively carried out with a heterogeneous catalyst that may be removed by filtration prior to fractionation and distillation of the final product.

The evaporation of water from the first reactor 102 (and from the second reactor 104 and the third reactor 106) drives the reaction to completion. As noted above, the semialdehyde, ketoacid, or ester thereof is generally added in excess to drive the reaction to completion. The excess semialdehyde, ketoacid, or ester thereof are however contaminants in the reaction product and therefore need to be removed. The recycling of the excess semialdehyde, ketoacid, or ester thereof facilitates completion of the reaction between the semialdehyde, ketoacid, or ester and the alcohol.

An exemplary separator 112 is a decanter. Other separators such as condensers, distillation columns, centrifuges, membrane filters, molecular sieves, and the like, can also be used.

In one embodiment, the first reactor 102 is maintained at a temperature of about 50 to about 150° C., specifically about 65 to about 130° C., and more specifically about 75 to about 120° C. during the reaction of the semialdehyde, ketoacid, or keto ester with the alcohol. In another embodiment, the first reactor 102 is maintained at a pressure of about 20 to about 760 millimeters (mm) of Mercury (Hg), specifically about 30 to about 700 mm Hg and more specifically about 40 to about 650 mm Hg. In yet another embodiment, the residence time for the reactants in the first reactor is about 3 to about 1200 minutes, specifically about 4 to about 180 minutes and more specifically about 5 to about 80 minutes.

In the first reactor 102, about 20 to about 95 mole percent, specifically about 50 to about 93 mole percent and more specifically about 75 to about 90 mole percent of the reactants are reacted to produce ketals or acetals.

The second reactor 104 and third reactor 106 are optional and are used to further remove any water byproducts. In an exemplary embodiment, the second reactor 104 and the third reactor 106 are primarily reactors with recirculating reboilers that are used to remove water from the reaction and some of the excess semi-aldehyde, ketoacid, or ester. Each of the second reactor 104 and the third reactor 106 are fitted with a second condenser 116 and a third condenser 118 respectively that facilitate further separation of the unreacted reactants from water by-product. The reactants are generally recycled to the first reactor 102.

In one embodiment, additional catalyst may be added to the second reactor 104 and to the third reactor 106 to facilitate an improved reaction between the semialdehydes, ketoacids and esters thereof with the alcohol. In an exemplary embodiment, the acid catalyst is added only to the first reactor 102.

In one embodiment, the temperature in the second reactor 104 and the third reactor 106 are maintained at temperatures of about 50 to about 150° C., specifically about 65 to about 130° C., and more specifically about 75 to about 120° C. respectively. In another embodiment, the second reactor 104 and the third reactor 106 are both maintained at pressures of about 5 to about 760 millimeters (mm) of Mercury (Hg), specifically about 8 to about 700 mm Hg and more specifically about 10 to about 50 mm Hg respectively. In yet another embodiment, the residence time for the reactants in the second and third reactor is about 3 minutes to about 1200 minutes, specifically about 4 to about 200 minutes and more specifically about 5 to about 80 minutes respectively.

In one embodiment, an amount of up to about 100 weight percent (wt %), specifically about 5 to about 90 wt %, and more specifically about 15 to about 50 wt % of the recycled semialdehydes, ketoacids and esters thereof, polyols, and ketal products are recycled to the first reactor 102. In one embodiment, when ethyl levulinate is reacted with glycerol to produce the glycerol ketal of ethyl levulinate, up to about 100 wt %, specifically about 50 to about 90 wt % of the excess ethyl levulinate added to the first reactor 102 can be removed after the reaction and recycled to the first reactor 102. A similar process is followed when propylene glycol is reacted with ethyl levulinate.

In an exemplary embodiment, the acid catalyst and other acid species (e.g., sulfur containing acid impurities) present in the product is removed by passing the reaction mixture stream through a bed 114. In one embodiment, the bed 114 is located downstream of the first, second or third reactors and upstream of the first and second distillation columns. The bed may also be located downstream of the first or second distillation columns 108 and 110 respectively.

It is desirable for the acetal or ketal product to contain less than or equal to about 0.001 to about 10 ppm sulfur-containing acid impurities, specifically about 0.002 to about 5 ppm sulfur-containing acid impurities, based on the total weight of the composition. The reduction in the amount of sulfur-containing acid impurities in the acetal or ketal product increases shelf life by increasing hydrolytic stability.

In one embodiment, in order to reduce the amount of sulfur-containing acid impurities present in the acetal or ketal product, the product is made to contact a base or buffer to neutralize any acid catalyst that is present prior to the first distillation column. In one embodiment, the acetal or ketal product contacts packed beds of bases/buffers to reduce sulfur-containing acid impurities and carboxylic acid impurities content to the desired levels. Examples of bases that can be used in packed beds are carbonates, amines, hydroxides, phosphates or oxides. An exemplary packed bed contains barium carbonate ($BaCO_3$). In another embodiment, the packed bed can comprise molecular sieves.

In another embodiment, the reactor product may be formulated with an inorganic salt that serves as a buffer. Other examples of buffers are solutions of citric acid, sodium citrate, sodium carbonate and sodium bicarbonate. Exemplary buffers are 0.1 molal (m) solutions of citric acid, sodium citrate, sodium carbonate, sodium bicarbonate, or a combination comprising at least one of the foregoing buffers.

By contacting the acetal or ketal product with a packed bed of molecular sieves, base or buffers, the product yield can be increased from about 75% to greater than 95% based upon the reactant feed. The product composition increases its shelf stability from less than 1 day to greater than at least 2 days, specifically greater than at least 1 week, and more specifically greater than at least 1 month.

In an exemplary embodiment, it is desirable for the glycerol ketal of ethyl levulinate composition to contain the sulfur-containing acid impurities in amounts of less than 20 ppm, specifically less than or equal to about 10 ppm and more specifically less than or equal to about 5 ppm, based on the total weight of the glycerol ketal of ethyl levulinate composition. In yet another exemplary embodiment, it is desirable for the propylene glycol ketal of ethyl levulinate composition to contain the sulfur-containing acid impurities in amounts of less than 20 ppm, specifically less than or equal to about 10 ppm and more specifically less than or equal to about 5 ppm, based on the total weight of the propylene glycol ketal of ethyl levulinate composition.

In an exemplary embodiment, it is desirable for the glycerol ketal of ethyl levulinate composition to have an acid number of less than 1, specifically less than 0.5, and more specifically less than 0.3, when measured as per ASTM D 664. In an exemplary embodiment, it is desirable for the propylene glycol ketal of ethyl levulinate composition to have an acid number of less than 1, specifically less than 0.5, and more specifically less than 0.3 when measured as per ASTM D 664.

The bed 114 can be a single bed or can comprise a plurality of beds. Examples of buffers or bases used in the bed are mono or di-basic sodium or potassium phosphates, mono, di- or tri-basic calcium or zinc phosphate, barium carbonate, barium phosphate, zinc carbonate, sodium carbonate, potassium carbonate, sodium citrate, potassium citrate, calcium citrate, basic alumina, a weakly basic anion exchange resin, etc. A partial acetal or ketal product (e.g., a product where the conversion is less than 95%) or a fully completed acetal or ketal product (e.g., a product where the conversion is greater than 95%) can contact the bed either in a single pass or in multiple passes.

In one embodiment, residual alcohol or polyol may be removed by passing the acetal or ketal product through a column or bed of ion exchange resin prior to distillation or post-distillation of the final ketal product of the alcohol. It is desirable for the ion exchange resin to contain sulfonate moieties. Without being limited by theory, it is believed that alcoholic compounds undergo hydrogen bonding with the sulfonate groups that are covalently bound to the matrix, and the alcohols are thereby removed from the reaction products. Examples of useful ion exchange resins include LEWATIT® 202 and/or LEWATIT® 405, sold by the Lanxess Company of Pittsburgh, Pa.; and AMBERLITE™ BD10DRY™, sold by the Rohm and Haas Company of Philadelphia, Pa. The period of contact of the acetal or ketal product with the column of ion exchange resin occurs for about 1 minute to about 5 hours, specifically about 10 minutes to about 3 hours and more specifically about 30 minutes to about 2 hours. The bed or column of the ion exchange resin can be a single bed or column or can be a series of beds or columns arranged in series or parallel.

The first distillation column 108 and the second distillation column 110 are used to reboil the reactants to perform a distillation to remove undesirable reactants (e.g., ketoester), byproducts (e.g., high molecular weight species) and residual catalyst (removed from an acid removal column and by distillation) from the ketal or acetal. In an exemplary embodiment, the first distillation column 108 is used to separate the ethyl levulinate from the glycerol ketal of ethyl levulinate product or the propylene glycol ketal of ethyl levulinate product.

In an exemplary embodiment, the glycerol ketal of ethyl levulinate product or the propylene glycol ketal of ethyl levulinate product is distilled in the first distillation column 108 and in the second distillation column second distillation column 110 to remove excess reactant (e.g., ethyl levulinate), high molecular weight species (e.g., dimers, trimers and oligomers) and acid catalyst to produce a purer form of the glycerol ketal of ethyl levulinate composition or the propylene ketal of ethyl levulinate composition. As stated above, the glycerol ketal of ethyl levulinate composition or the propylene ketal of ethyl levulinate composition each contain less than 2 wt % contaminants based on the total weight of the respective glycerol ketal of ethyl levulinate composition or the propylene glycol ketal of ethyl levulinate composition.

In one embodiment, the distillation column 108 is fitted with up to 6 theoretical stages (also termed "stripping stages or rectification stages" or "trays"). The trays at the top of the first distillation column are maintained at a temperature of about 40 to about 170, specifically about 65 to about 120° C., while the trays at the bottom of the first distillation column are maintained at a temperature of about 100 to about 200° C., specifically about 120 to about 180° C., and more specifically about 140 to about 160° C. The pressure at the bottom of the first distillation column is about 5 to about 760 mm Hg, specifically about 10 to about 500 mm Hg, and more specifically about 15 to about 50 mm Hg. The reflux to feed ratio in the first distillation column can be up to about 1.0 and specifically about 0 to about 0.5.

In one embodiment, in the fractionation step, excess ethyl levulinate and polyol is stripped using a strong vacuum of about 0.5 to about 20 mm Hg. The stripping tower uses a strong vacuum as the glycerol ketal of ethyl levulinate essentially needs to boil in order to reach low levels of ethyl levulinate. If the temperature in the distillation column is too high, the ketal product is lost to oligomers or other by-products. Similarly, if the tower packing is too tall or the pressure drop is too high due to the type of packing, the glycerol ketal of ethyl levulinate cannot be produced to the purity required in many of its applications.

Various types of packing can be used in the first distillation columns—BX, BX Plus, MELLAPAK, FLEXIPAC, mesh, or similar structured packing that have low (Height Equivalent to the Theoretical Plate) HETP combined with low pressure drop per unit height. The HETP varies from about 6 inches to about 24 inches, specifically about 9 inches to about 15 inches.

The second distillation column 110 functions to deliver a ketal or acetal product that meets desired criteria for chemical stability. The second distillation column 110 functions primarily to remove high molecular weight species and other contaminants that reduce chemical stability, change color or promote changes in viscosity over time. As noted above, it is desirable to obtain a product that has a long shelf life. By "long shelf life," it is meant that the product does not undergo changes in molecular weight, changes in composition, or changes in color over extended periods of time (e.g., about 12 hours to about 12 months).

The stages at the bottom of the second distillation column are maintained at temperatures of about 70 to about 300° C., specifically about 120 to about 200° C., and more specifically about 140 to about 160° C. The pressure at the bottom of the distillation column is about 5 to about 760 mm Hg, specifically about 10 to about 500 mm Hg, and more specifically about 15 to about 50 mm Hg. In an exemplary embodiment, the temperature at the bottom of the second distillation column is about 140 to about 200° C., while the pressure is about 5 to about 50 mm Hg. The reflux to feed ratio in the second distillation column for the second distillation column is about 0.1 to about 3.0 and specifically about 0.5 to about 2.0.

A single flash is generally not effective in purifying glycerol ketal of ethyl levulinate or the propylene glycol ketal of ethyl levulinate from the oligomeric species that accumulate in the reactors and in the first distillation column. In one embodiment, two or more stages and a reflux are used to keep the higher molecular weight species out of the ketal or acetal product. Downstream applications are affected if the higher molecular weight species are not removed, due to the presence of low levels of color-forming bodies.

The number of stripping stages can be any number greater than 1, specifically greater than 2, and more specifically greater than 4. The number of rectification stages is greater than or equal to about 1, and specifically greater than or equal to about 2. In an exemplary embodiment, the number of stripping stages is greater than or equal to about 4, while the number of rectification stages is greater than or equal to about 2.

In one embodiment, the bottom of the first distillation column and the bottom of the second distillation column can be purged to remove the "heavy species" (e.g., high molecular weight species, dark-colored species, and carboxylic acids, unwanted acid catalyst and catalyst by-products). The temperature at the bottom of the distillation column is maintained at a temperature of less than or equal to about 250° C., specifically less than or equal to about 200° C., and more specifically less than or equal to about 180° C. to prevent degradation of the distillate that remains at the bottom of the column. In one embodiment, when the final product is a glycerol ketal of ethyl levulinate composition, the temperature at the bottom of the distillation column is about 120 to about 200° C. In another embodiment, when the final product is a propylene glycol ketal of ethyl levulinate composition, the temperature at the bottom of the distillation column is about 100 to about 180° C. The high molecular weight species and unwanted catalyst are removed from the distillation column and discharged to a drain or to a waste tank.

The distillation of the final ketal product or the excess reactant can also be carried out with wiped film evaporators, spinning film evaporators, rotary evaporators, falling film evaporators and other similar equipment. In one embodiment, the ketal or acetal may be removed to a small extent in the first distillation column and subsequently re-used by mixing with additional fresh reactants.

In producing the glycerol ketal of ethyl levulinate composition or the propylene glycol ketal of ethyl levulinate composition, it is desirable to use reaction conditions that permit conversions of greater than or equal to about 90 mole percent and specifically greater than or equal to about 95 mole percent of the alcohol, specifically the glycerol. Unreacted glycerol that is present in the composition in amounts of greater than about 5000 ppm is problematic to the quality of the products because of inherent functionality of the glycerol (3 hydroxyl groups), the insoluble nature of glycerol (may cause cloudiness when in contact with organic solutions), and the hygroscopic nature of glycerol. Glycerol should be present in amounts of less than or equal to about 10,000 parts per million (ppm), specifically about 1 to about 8,000 ppm and more specifically about 2 to about 5,000 ppm, based on the total weight of the glycerol ketal of ethyl levulinate composition. Similarly, propylene glycols should be present in amounts of less than or equal to about 10,000 parts per million (ppm), specifically about 1 to about 8,000 ppm and more specifically about 2 to about 5,000 ppm, based on the total weight of the propylene glycol ketal of ethyl levulinate composition.

In one embodiment, the glycerol ketal of ethyl levulinate composition or the propylene glycol ketal of ethyl levulinate comprises less than 2 wt % contaminants, specifically less than or equal to about 1.75 wt % contaminants, specifically less than or equal to about 1.5 wt % contaminants, specifically less than or equal to about 1.25 wt % contaminants, specifically less than or equal to about 1 wt % contaminants, specifically less than or equal to about 0.75 wt % contaminants, specifically less than or equal to about 0.5 wt % contaminants and more specifically less than or equal to about 0.25 wt % contaminants. The contaminants are unreacted semialdehydes, ketoacids or esters thereof, unreacted alcohol, the catalyst, sulfur-containing acid impurities, carboxylic acid impurities, and high molecular weight species such as dimers, trimers and oligomers produced by an aldol reaction between the ketal or acetal and ethyl levulinate, a reaction between the semialdehydes, ketoacids or esters thereof and the ketal or acetal, a reaction between the semialdehydes, ketoacids or esters thereof and an aldol of the ketal or acetal, or a reaction between the semialdehydes, ketoacids or esters thereof, the aldol of the ketal or acetal, and the ketal or acetal.

It is desirable to reduce the amount of residual alcohol or polyol to less than 7500 ppm, specifically less than or equal to about 5000 ppm and more specifically less than or equal to about 2000 ppm, based on the weight of acetal or ketal product.

In an exemplary embodiment, it is desirable for the glycerol ketal of ethyl levulinate composition to contain glycerol in amounts of less than 7500 ppm, specifically less than or equal to about 5000 ppm and more specifically less than or equal to about 2000 ppm, based on the total weight of the glycerol ketal of ethyl levulinate composition. In yet another exemplary embodiment, it is desirable for the propylene glycol ketal of ethyl levulinate composition to contain propylene glycol in amounts of less than 5000 ppm, specifically less than or equal to about 2000 ppm and more specifically less than or equal to about 1000 ppm, based on the total weight of the propylene glycol ketal of ethyl levulinate composition.

It is also desirable to reduce the amount of water present in the acetal or ketal product to less than or equal to about 2000 ppm, specifically less than or equal to about 1000 ppm, and more specifically less than or equal to about 500 ppm based on the weight of acetal or ketal product. The water may be removed by sparging the product with hot dry nitrogen having less than 100 ppm. Vacuum traps may be used in conjunctions with either of the reactors 102, 104, 106 or in conjunctions with the distillation columns 108, 110 to remove water. In one embodiment, in order to improve performance of the system 100, a cold trap operating at a temperature of −60° C. or a condenser that operates at a temperature of below 50° F. may be used to remove water present in the acetal or ketal product.

In one embodiment, when ethyl levulinate is reacted with glycerol to obtain the glycerol ketal of ethyl levulinate composition, it is desirable for the glycerol ketal of ethyl levulinate composition to contain less than 500 ppm water, specifically less than or equal to about 250 ppm water and specifically less than or equal to about 150 ppm water, based on the total weight of the glycerol ketal of ethyl levulinate composition. The glycerol ketal of ethyl levulinate composition may contain less than or equal to about 10,000 ppm, specifically less than or equal to about 5,000 ppm and more specifically less than or equal to about 2,000 ppm of the glycerol, based on the total weight of the glycerol ketal of ethyl levulinate composition.

In another embodiment, when ethyl levulinate is reacted with propylene glycol to obtain the propylene glycol ketal of ethyl levulinate composition, it is desirable for the propylene glycol ketal of ethyl levulinate composition to contain less than 500 ppm water, specifically less than or equal to about 250 ppm water and specifically less than or equal to about 150 ppm water, based on the total weight of the propylene glycol ketal of ethyl levulinate composition. The propylene glycol ketal of ethyl levulinate composition may contain less than or equal to about 5,000 ppm, specifically less than or equal to about 3,000 ppm and more specifically less than or equal to about 2,000 ppm of the propylene glycol, based on the total weight of the propylene glycol ketal of ethyl levulinate composition.

In yet another embodiment, the glycerol ketal of ethyl levulinate composition or the propylene glycol ketal of ethyl levulinate composition comprises less than or equal to about 1 wt % ethyl levulinate, specifically less than or equal to about 0.5 wt % ethyl levulinate, and more specifically less than or equal to about 0.2 wt % ethyl levulinate, based on the total weight of the respective compositions.

In one embodiment, the glycerol ketal of ethyl levulinate composition may contain less than or equal to about 0.5 wt %, specifically less than or equal to about 0.2 wt % of dimers obtained from a reaction between the glycerol ketals of ethyl levulinate. In yet another embodiment, the glycerol ketal of ethyl levulinate composition may contain less than 1 wt %, and specifically less than or equal to about 0.2 wt %, and more specifically less than or equal to about 0.1 wt % of dimers obtained from an aldol reaction between the glycerol ketal of ethyl levulinate and ethyl levulinate. In yet another embodiment, the glycerol ketal of ethyl levulinate composition may contain less than 0.5 wt %, and specifically less than or equal to about 0.25 wt %, and more specifically less than or equal to about 0.1 wt % of dimers obtained from a reaction between the glycerol ketals of ethyl levulinate and ethyl levulinate.

In another embodiment, the glycerol ketal of ethyl levulinate composition may contain less than or equal to about 0.5 wt % trimers, and specifically less than or equal to about 0.2 wt % of trimers obtained from a reaction between the glycerol ketals of ethyl levulinate. In yet another embodiment, the glycerol ketal of ethyl levulinate composition may contain less than or equal to about 0.5 wt % trimers, and specifically less than or equal to about 0.2 wt % of trimers obtained from an aldol reaction between the glycerol ketal of ethyl levulinate and the dimer reaction product of the glycerol ketal of ethyl levulinate and ethyl levulinate. In yet another embodiment, the glycerol ketal of ethyl levulinate composition may contain less than or equal to about 0.5 wt % trimers, and specifically less than or equal to about 0.2 wt % of trimers obtained from a reaction between the glycerol ketals of ethyl levulinate and ethyl levulinate.

In one embodiment, the glycerol ketal of ethyl levulinate composition may contain less than or equal to about 0.20 wt % tetramers, and specifically less than or equal to about 0.1 wt % of tetramers obtained from a reaction between glycerol ketal of ethyl levulinate and ethyl levulinate or from a reaction between glycerol ketal of ethyl levulinate and itself. All weight percents listed above for the byproducts of the reaction between the glycerol and the ethyl levulinate are based on the total weight of the glycerol ketal of ethyl levulinate composition.

In another embodiment, the propylene glycol ketal of ethyl levulinate composition may contain less than or equal to about 0.5 wt %, specifically less than or equal to about 0.2 wt % of dimers obtained from a reaction between ethyl levulinate and the propylene glycol ketal of ethyl levulinate. In yet another embodiment, the propylene glycol ketal of ethyl levulinate composition may contain less than 1 wt %, and specifically less than or equal to about 0.5 wt %, and more specifically less than or equal to about 0.2 wt % of dimers obtained from an aldol reaction between the propylene glycol ketal of ethyl levulinate and ethyl levulinate.

In another embodiment, the propylene glycol ketal of ethyl levulinate composition may contain less than or equal to about 0.2 wt % oligomers derived from the reaction between two molecules of ethyl levulinate and 1 molecule of propylene glycol (trans-esterification to produce a di-ester). In yet another embodiment, the propylene glycol ketal of ethyl levulinate composition may contain less than or equal to about 0.2 wt % oligomers derived from the reaction between two molecules of the propylene glycol ketal of ethyl levulinate and 1 molecule of propylene glycol (trans-esterification to produce a di-ketal-di-ester), and specifically less than or equal to about 0.1 wt % of oligomers derived from the reaction between two molecules of the propylene glycol ketal of ethyl levulinate and 1 molecule of propylene glycol (trans-esterification to produce a di-ketal-di-ester).

All weight percents listed above for the byproducts of the reaction between the propylene glycol and the ethyl levulinate are based on the total weight of the propylene glycol ketal of ethyl levulinate composition. All weight percents listed above for the byproducts of the reaction between the glycerol ketal and the ethyl levulinate are based on the total weight of the glycerol ketal of ethyl levulinate composition.

In one embodiment, the propylene glycol ketal of ethyl levulinate composition or the glycerol ketal of ethyl levulinate composition may be hydrogenated.

Ketals or acetals produced by the aforementioned process are thermally and color stable. In one embodiment, when subjected to temperatures of about 200° C. for a period of a few hours, the color change is less than 30 YI units. In another embodiment, when subjected to temperatures of about 200° C. for a period of a few hours, the color change is less than 1 index of absorption unit. In another embodiment, when subjected to a UV chamber for a period of at least 2 days, the color change is less than 1 index of absorption unit. Ketals or acetals produced by this process are also shelf stable and hydrolytically stable.

As noted above, it is desirable for the acetals or ketals to be hydrolytically stable (i.e., to be hydrostable). A desirable hydrostability for the acetals of ketals disclosed herein is displaying a retention in chemical composition of greater than or equal to about 70 weight % after exposure to water for about 24 hours at a temperature of about 65° C. as determined by GC-FID. Materials of the invention display retention in chemical composition of greater than or equal to about 70 weight % after exposure to water for about 24 hours at a temperature of about 65° C. as determined by GC-FID. In order to determine the hydrostability, the chemical composition of a given acetal or ketal composition is first determined by GC-FID. A sample of this composition is placed into a glass scintillation vial and a certain amount of water is added. Optionally, an added reagent or buffer can be added into the vial. The vial is then sealed and placed into a hot-air oven for 24 hour at about 65 to about 70° C. After 24 hour, an aliquot is removed and analyzed by GC-FID.

Shelf-stability is defined as an acetal or ketal composition that has less than or equal to about 0.5 wt % purity change from its original chemical purity after aging for 20 hours at 20° C. from production as determined by GC-FID. The chemical purity of the compound was determined by GC-FID with an internal standard and calibration curve.

Color stability is defined as a change of less than 1 index of absorption unit (IAU) after subjecting a reagent to heat, UV light, or room temperature aging. An IAU is equal to the number of area units calculated by integrating the area under the UV spectrum curve of a compound from 380 nm to 500 nm using an ultraviolet-visible detector and a quartz cell that is 10 mm in diameter. The sample may be diluted in a non-UV absorbing solvent (no absorption between 380-500 nm wavelength), such as methanol, water, or another solvent prior to the UV-VIS measurement in order to measure the area under the curve corresponding to IAU. A blank UV spectrum is performed on the solvent before measuring the sample dissolved in solvent.

An IAU measurement may also be used to detect the amount of yellowness of liquid samples in a neat form or dissolved in solvent that does not absorb in the UV spectrum between 380-500 nm. In this case, an IAU less than or equal to about 0.1 is desirable for low yellowness color.

The presence of unknown UV-absorbing impurities may also be detected by liquid chromatography, for example, HPLC. The HPLC is used in conjunction with a UV detector to analyze for UV-absorbing impurities that are structurally different and separated chromatographically from the ketal product. These unknown impurities have a UV absorbance peak, which one integrates the area under the peak to calculate the relative amount of UV-absorbing impurity within a given composition. The lower the area under the curve of these UV absorbing impurities indicates that the ketal composition is subsequently more pure and free from possible color-body impurities. These unknown impurities can lead to quality problems, for example, thermal, UV, and color stability.

The ketals or acetals can be used in a variety of articles such as personal care products such as shampoos, lotions, shaving creams, deodorants, lipstick, makeup, makeup remover, hair dye and the like as well as industrial products such as paints, inks, paint strippers, fabric softeners, laundry detergents, candles, polymeric products that contain compatibilizers such as exterior body panels for automobiles, exterior surfaces of electronics goods, and the like. In one embodiment, the ketals or acetals may be converted into a polymer that is used as a plasticizer, a toughener, a surfactant, a barrier layer compound, an interfacial modifier, a compatibilizer, or a phase transfer compound.

EXAMPLES

Examples 1-12

These examples were conducted to demonstrate the manufacturing of high purity (greater than 99%) propylene glycol ketal of ethyl levulinate and the glycerol ketal of ethyl levulinate. In particular, these examples demonstrate a continuous and batch purification process for propylene glycol ketal of ethyl levulinate and the glycerol ketal of ethyl levulinate. These examples also demonstrate that continuously purging the strong acid catalyst from the bottoms of the distillation column (especially the bottoms of the second distillation column) can be used to obtain high purity propylene glycol ketal of ethyl levulinate and the glycerol ketal of ethyl levulinate. The examples also surprisingly demonstrate that treatment of the product with certain inorganic compounds before or after distillation increases chemical stability. The compositions made using specific sulfur-based catalyst were also found to be chemically stable.

The method was conducted as follows. A reaction mixture comprising water, propylene glycol ketal of ethyl levulinate, ethyl levulinate, propylene glycol, a homogeneous acid catalyst, and other impurities were fed into a first distillation column. The compositions for all of the examples and the comparative examples are shown in the Table 1 below. All of the examples and comparative examples contain a homogeneous catalyst except for the examples 7 and 8, which were manufactured using a heterogeneous catalyst.

Low boiling impurities were first removed from the reaction mixture via distillation. Concentrated propylene glycol ketal of ethyl levulinate, higher boiling impurities and remaining acid catalyst were then fed into a second distillation column. In the second distillation column, propylene glycol ketal of ethyl levulinate was removed overhead while the homogeneous acid catalyst was continuously purged from the bottom of the second distillation column. The propylene glycol ketal of ethyl levulinate obtained from overhead distillation in the second distillation column was over 99% pure as shown in the Table 1 below.

In the following Examples 1-12, propylene glycol ketal of ethyl levulinate having the Formula 7 shown below and glycerol ketal of ethyl levulinate having the Formula 8 shown below were manufactured.

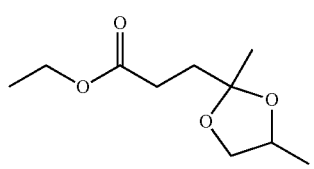

(7)

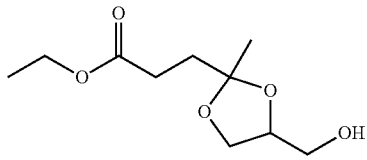

(8)

Examples 1 and 2

Into a CSTR was continuously and simultaneously charged propylene glycol (21 wt % of total composition) and ethyl levulinate (79 wt % of total composition). An aqueous solution of sulfuric acid was continuously pumped into the CSTR at 20-60 parts per million of the total composition weight. The CSTR was at a temperature of 95° C. and a pressure of 80 mm Hg. The reagents were converted into 7, and water was continuously removed from the CSTR. The composition of the overheads also contained propylene glycol and ethyl levulinate. The flow rate out of the reactor was 58 lbs/hour. The CSTR product was discharged into a second reactor, and was heated to 100° C. and a vacuum pressure of 61 mm Hg. The reagents were further converted into a propylene glycol ketal of ethyl levulinate (having Formula 7), and water was continuously removed from the second reactor. The flow rate of product from the first reactor into the second reactor was 61 lbs/hour. The second reactor discharged the product into a third reactor, and the product was heated to 106° C. and a vacuum pressure of 30 mm mercury (Hg). The composition of the reaction mixture at the end of the third reactor comprised 0.049 wt % water, 0.27 wt % propylene glycol, 46.25 wt % ethyl levulinate, 53.05 wt % propylene glycol ketal of ethyl levulinate and 0.44 wt % of other impurities, including the transesterification condensation product of propylene glycol and the propylene glycol ketal of ethyl levulinate.

The composition was then fed into a first distillation column at a temperature between 90 to 110° C. at a rate of 60 to 80 lbs/hour. The overhead vacuum on the distillation column was 5 to 10 mm Hg. The composition was refluxed in the column and re-circulated in the bottom of the distillation column in a reboiler at a temperature of 100 to 130° C. The composition was then fed into a second distillation column at a temperature between 100 to 120° C. at a rate of 20 to 40 lbs/hour. The overhead vacuum on the column was 5 to 10 mm Hg. The composition was refluxed in the column and recirculated in the bottom of the distillation column in a reboiler at a temperature of 80 to 100° C., distilled overhead, and collected. During the distillation, the bottoms of the distillation column were purged out at a rate of 3 lbs/hour. The final composition of the distilled product comprised 99.8% propylene glycol ketal of ethyl levulinate. A small sample of the distilled product 7 was put into a scintillation vial and stored at room temperature to test its shelf stability. After 14 days a sample was taken out of the scintillation vial and analyzed by GC-FID. The results of analysis are shown in Table 1.

The procedure of the process to make Example 1 was repeated for Example 2.

Examples 3-5

The procedure of the process to make Example 1 was repeated except that prior to distillation, the reaction mixture that exited the third reactor was flowed through a packed bed of solid barium carbonate. After exiting the packed bed, the mixture was then distilled as described in Example 1. Small samples of the distilled composition 7 were put into separate scintillation vials and stored at room temperature to test the example's shelf stability. After 13 days a sample was taken out of the scintillation vial and analyzed by GC-FID. The results of analysis are shown in Table 1

Example 6

A 500 mL 3-neck round bottom flask was charged with 45.72 grams (g) (0.50 mol) glycerol (99+% purity), 215.24 g (1.50 mol) ethyl levulinate (98+% purity), 0.0138 g (50 ppm) 2-Naphthalenesulfonic acid (obtained from TCI America) and a magnetic stir bar. The flask was equipped with a thermocouple, heat tape wrapped dean stark, condenser, glass stopper and an outlet to the vacuum. The contents of the flask were heated to 110° C. using a heating mantle. The vacuum gauge was set to start at a vacuum pressure of 300 torr with a ramp rate of 300 torr/hour and end at 30 torr. Once the pot temperature reached 110° C. the reaction mixture turned from cloudy to clear and then the Teflon vacuum pump was turned on and the vacuum was immediately applied to the system. After a total reaction time of 60 minutes the heat was turned off and the flask was backfilled with nitrogen. The reaction mixture was then charged with 26 g (10 wt %) dibasic sodium phosphate and heated at 60° C. for 1 hour, then filtered. The mixture was charged into a 500 ml 4-neck round bottom flask equipped with a stir bar. The flask was equipped with a thermocouple, 2 glass stoppers, vigreux column, short path condenser, adapter and three collection flasks. The vacuum was set to 5.0 torr, and the flask was heated to effect distillation. The excess ethyl levulinate was distilled out first and then the composition 8 was distilled. A sample of the distilled product was analyzed by GC-FID. A small sample of the distilled product 8 was put into a scintillation vial and stored at room temperature to test its shelf stability. After four days a sample was taken out of the scintillation vial and analyzed by GC-FID. The results of analysis are shown in Table 1.

Example 7

Into a CSTR was continuously and simultaneously charged glycerol (18 wt % of total composition) and ethyl levulinate (82 wt % of total composition). An aqueous solution of sulfuric acid was continuously pumped into the CSTR at 20-60 parts per million of the total composition. The CSTR was at a temperature of 85-93° C. and a pressure of 70-80 mm Hg. The reagents were converted into product 8, and water was continuously removed from the CSTR. The flow rate through the CSTR was between 70-90 lbs/hour. The CSTR contents were then discharged into a second reactor, and heated to 94-100° C. and a vacuum pressure of 30 mm Hg. The reagents were further converted into 8, and water was continuously removed from the CSTR. The flow rate through the second reactor was between 60-80 lbs/hour. The second reactor contents were discharged into a third reactor, and heated to 98-105° C. and a vacuum pressure of 20-25 mm Hg. The composition of the reaction mixture at the end of the third reactor was 0.13 wt % glycerol, 47 wt % ethyl levulinate, 50.9 wt % glycerol ketal of ethyl levulinate, 1.72 wt % of higher molecular weight condensation products, such as those described above in the specification and 0.22 wt % of other impurities. The composition 8 was fed into the first distillation column at a temperature between 90 to 110° C. at a rate of 40 to 50 lbs/hour. The overhead vacuum on the distillation column was 5 to 10 mm Hg. The mixture was refluxed in the column and re-circulated in the bottom of the distillation column in a re-boiler at a temperature of 150 to 160° C. The composition was subsequently fed into a second distillation column at a temperature between 130 to 140° C. at a rate of 30 to 35 lbs/hour. The overhead vacuum on the column was 4 to 8 mm Hg. The mixture was refluxed in the column and re-circulated in the bottom of the distillation column in a re-boiler at a temperature of 170 to 180° C., distilled overhead, and collected. A sample of this condensate containing 8, was redistilled by fractional distillation to a composition of 99.6% purity. The sample was split into 2 fractions. The first was stored in a capped round bottom flask for 7 days at room temperature. A GC-FID measurement of the composition was performed after aging. The results are shown in Table I. The second fraction is described below in Example 8.

Example 8

The second fraction from Example 7 was immediately treated with 10 wt % slurry of barium carbonate and filtered. The contents were put into a glass scintillation vial and stored for 9 days at room temperature. A GC-FID measurement of the composition was performed after aging. The results are shown in Table I.

Example 9

Example 6 was repeated except 50 ppm of (1R)-(−)-10-Camphorsulfonic acid (CSA) was used as the catalyst instead of 2-NSA and the reaction product was not treated with anything prior to distillation purification of 8. The contents were put into a glass scintillation vial and stored for 7 days at room temperature. A GC-FID measurement of the composition was performed after aging. The results are shown in Table I.

Example 10

Example 9 was repeated and the distilled product 8, was subsequently treated with 10 wt % barium carbonate and filtered. The contents were put into a glass scintillation vial and stored for 7 days at room temperature. A GC-FID measurement of the composition was performed after aging. The results are shown in Table I.

Example 11

Example 6 was repeated except 0.23 wt % of Nafion® SAC-13 was used as the catalyst instead of 2-NSA, the catalyst was filtered prior to distillation, and the reaction product was not treated with anything prior to distillation of 8. After distillation, the contents were put into a glass scintillation vial and stored for 3 days at room temperature. A GC-FID measurement of the composition was performed after aging. The results are shown in Table I.

Example 12

The procedure used in Example 11 was repeated except that 0.23 wt % Amberlyst® 35 was used as the catalyst. After distillation, the contents were put into a glass scintillation vial and stored for 10 days at room temperature. A GC-FID measurement of the composition was performed after aging. The results are shown in Table I.

TABLE I

| Example | Reagent Formula | Purity of Reagent after distillation | Ketalization catalyst | Pre-Distillation Treatment with Inorganic Compound/Mixture | Purity after test | Time of Test (days) | Temp. of Test (° C.) |
|---|---|---|---|---|---|---|---|
| Example 1 | 7 | 99.8 | $H_2SO_4$ | none | 99.5 | 14 | 20 |
| Example 2 | 7 | 99.6 | $H_2SO_4$ | none | 99.2 | 14 | 20 |
| Example 3 | 7 | 99.9 | $H_2SO_4$ | $BaCO_3$ | 99.9 | 13 | 20 |
| Example 4 | 7 | 99.8 | $H_2SO_4$ | $BaCO_3$ | 99.8 | 13 | 20 |
| Example 5 | 7 | 99.8 | $H_2SO_4$ | $BaCO_3$ | 99.7 | 13 | 20 |
| Example 6 | 8 | 99.8 | 2-NSA | Dibasic Na Phosphate | 98.2 | 4 | 20 |
| Example 7 | 8 | 99.6 | $H_2SO_4$ | none | 98.4 | 7 | 20 |
| Example 8 | 8 | 99.6 | $H_2SO_4$ | $BaCO_3$ | 99.4 | 9 | 20 |
| Example 9 | 8 | 99.6 | CSA | none | 99.3 | 7 | 20 |
| Example 10 | 8 | 99.6 | CSA | $BaCO_3$ | 99.3 | 7 | 20 |
| Example 11 | 8 | 99.3 | Nafion ® SAC-13 | none | 99.3 | 3 | 20 |
| Example 12 | 8 | 99.2 | Amberlyst ® 35 | none | 99.2 | 10 | 20 |

2-NSA = 2-napthalene sulfonic acid
CSA = camphor sulfonic acid

Each of the Examples in the Table I showed good shelf stability. Those materials that were treated with an inorganic material showed even better shelf stability. The use of barium carbonate as a base to remove sulfur-based catalysts aided in the development of shelf-stable ketal-esters. The compositions (from the comparative examples) which were either not passed through the bed of barium carbonate or were passed through an alternative bed of dibasic sodium phosphate showed a slight change in chemical purity, while those compositions which passed through the bed of barium carbonate showed no change in chemical purity after a period of about 3 to about 14 days. The use of camphor-sulfonic acid as the sulfur-based catalyst produced more shelf-stable ketal-esters. The heterogeneous ketalization catalysts (Examples 11-12) also showed good shelf-stability.

Example 13-16

The starting reagent for all of the examples in Table 2 was manufactured according to Example 7 above. The final distilled composition of 8 was subsequently redistilled (fractionally) as described in Example 7 to a purity of 99.1%.

These examples were conducted to demonstrate that certain slurried or packed beds of materials functioned to aid in the shelf stability of the final ketal product compositions with regards to reformation of reactants. The reagent purity was 99.1% purity as determined by GC-FID, and the amount of ketal starting reagents, ethyl levulinate and glycerol, were quantified by GC-FID. The sample was analyzed by GC-FID within 5 hours after collection, and then it was split into 4 separate samples. One sample was placed into a glass vial and capped (Example 13). The other 3 samples (Examples 14-16) were treated with various reagents disclosed in Table 2. After 24 hours of aging from the time the first sample was collected from the distillation column, glycerol ketal of ethyl levulinate was analyzed again by GC-FID to determine the amount of ketal degradation products (glycerol and ethyl levulinate reactants) that had formed while sitting on the shelf.

TABLE 2

| Example | Amount of ethyl levulinate + glycerol before aging | Treatment Method | Amount of ethyl-levulinate and glycerol after aging | % Increase in ethyl levulinate and glycerol upon aging | Temperature of Aging |
|---|---|---|---|---|---|
| Example 13 | 0.46 | none | 0.96 | 106 | 20 |
| Example 14 | 0.46 | dibasic sodium phosphate | 0.70 | 51 | 20 |
| Example 15 | 0.46 | tribasic potassium phosphate | 0.49 | 5 | 20 |
| Example 16 | 0.46 | Class 4A Molecular Sieves | 0.54 | 17 | 20 |

As can be seen from Table 2, the treatment of the final distilled ketal product by a phosphate compound or by molecular sieves allowed the product to be more shelf stable as indicated by the lower percent increase in reformation of reactants, glycerol and ethyl levulinate. Without being bound by theory, it is believed that the treatment methods aided in disallowing residual impurities from the catalyst or side-products to catalyze the reformation reactions.

Examples 17-20

These examples were conducted to demonstrate the hydrostability of propylene glycol ketal of ethyl levulinate and glycerol ketal of ethyl levulinate when exposed to water at elevated temperatures. These examples also demonstrate that buffers can be used to chemically stabilize the ketals shown in Table 3 below. Each of the examples in Table 3 comprising 7 were manufactured according to Example 1. Each of the examples in Table 3 comprising 8 were manufactured according to Example 7. The compositions of the samples subjected to these experiments are similar to that described in the Examples 1-12 above.

A hydrostability study was conducted to analyze the stability of the ketal reagents toward water at elevated temperature. The reagents were charged into glass scintillation vials with water and optionally, a buffer system, and capped. Citric acid was used as the buffer. The vials were placed in an oven at 68° C. and removed after 24 hours of aging. A GC-FID was performed to analyze for the amount of ketal reagent after the hydrolytic stability test.

TABLE 3

| Example | Formula 8 (%) | Formula 7 (%) | Water (%) | pH of Water solution | Citric acid (phr) in water | Na Citrate (phr) in water | % Ketal Remaining after 24 h at 68° C. |
|---|---|---|---|---|---|---|---|
| Example 17 | 0 | 10 | 90 | 8 | $3.9 \times 10^{-4}$ | 0.29 | 96 |
| Example 18 | 0 | 10 | 90 | 6.8-7.0 | 0 | 0 | 76 |
| Example 19 | 10 | 0 | 90 | 8 | $3.9 \times 10^{-4}$ | 0.29 | 85 |
| Example 20 | 10 | 0 | 90 | 6.8-7.0 | 0 | 0 | 3 |

As can be seen from the Table 3, the ketals of Formulas 7 and 8 have improved hydrostability with the addition of citric acid/salt buffer reagents. Besides citrate buffers, phosphate and other multi-functional carboxylate buffer systems work to aid in the ketal stability compared to ketal compositions not containing buffer.

Examples 21-27

The synthesis and purification of the compound of Formula 8 (glycerol ketal of ethyl levulinate) was conducted in these examples.

Example 21 was made according to Example 6.

Example 22 was made according to Example 7 except that product 8 was only distilled one time.

Example 23 was made by hydrogenating Example 22 in a Parr reactor with 1 wt % Ni 5249P (BASF) at 400 psi $H_2$ and 140 deg C. for 4 h.

Example 24 was made according to Example 7.

Example 25 was made according to Example 7 except that one additional distillation was performed.

Example 26 was made according to Example 11.

Example 27 was made according to Example 12.

Examples 21 and 22 were examined for residual sulfur (S) content in the final distilled product, and were found to contain high amounts of sulfur compared to Examples 23 through 27. Various treatment methods or using alternative sulfur-based catalysts resulted in lower amounts of sulfur in the final product.

TABLE 4

| Example | Ketal formula | Ketalization Catalyst | Treatment Method | S (ppm) in Ketal |
|---|---|---|---|---|
| Example 21 | 8 | PTSA | none | 41.1 |
| Example 22 | 8 | $H_2SO_4$ | none | 11.4 |
| Example 23 | 8 | $H_2SO_4$ | $H_2$, Ni cat. | 2.2 |
| Example 24 | 8 | $H_2SO_4$ | 1 additional fractional distillation | 3.7 |
| Example 25 | 8 | $H_2SO_4$ | 2 additional fractional distillations | 1.2 |
| Example 26 | 8 | NAFION ® | none | 0.5 |
| Example 27 | 8 | AMBERLYST 15 ® | none | 0.8 |

Sulfur impurities are generally detrimental to products, especially renewable products. They are known to cause odor, color, and stability problems. Limitation of sulfur below 10 ppm, preferably below 8 ppm, and more preferable below 5 ppm are desirable.

In summary, from the foregoing Examples 1-27 it may be seen that a continuous purification process for propylene glycol ketal of ethyl levulinate and glycerol ketal of ethyl levulinate has been demonstrated.

Examples 28-33

Examples 28 and 29 include no purging of distillation bottoms. The positive effect of the purging of the distillation bottoms was previously demonstrated in Examples 1-2.

For Examples 28 and 29, the method used to synthesize the propylene glycol ketal of ethyl levulinate was previously described Example 1 except without the purge of the bottoms of the last distillation column. The details of the purification process were as follows. Into a middle zone of a distillation column was fed a reaction composition comprising 0.1 wt % water, 0.8 wt % propylene glycol, 37.7 wt % ethyl levulinate, 60.9 wt % propylene glycol ketal of ethyl levulinate and 0.6 wt % of other impurities. The composition was fed into the first distillation column at a temperature between 90 to 110° C. at a rate of 60 to 80 lbs/hour. The overhead vacuum on the distillation column was 5 to 10 mm of Hg. The mixture was refluxed in the column and recirculated to the bottom of the distillation column in a reboiler at a temperature of 100 to 130° C.

Then, the composition was fed into a second distillation column at a temperature between 100 to 120° C. at a rate of 20 to 40 lbs/hour. The overhead vacuum on the column was 5 to 10 mm Hg. The mixture was refluxed in the column and recirculated in the bottom of the distillation column in a reboiler at a temperature of 80 to 100° C., distilled overhead, and collected into a stainless steel container. The final composition of the distilled product comprised 243 ppm water, 0.4 wt % propylene glycol, 1.2 wt % ethyl levulinate, 98.3 wt % propylene glycol ketal of ethyl levulinate and 0.01 wt % of other impurities. The compositions for Examples 28 and 29 are shown in the Table 5 below.

Each of the examples 30-33 were synthesized according to Example 1 (3 reactor system in series with similar parameters of operation). The following details about the distillation purification were as follows: Into a middle zone of a distillation column was continuously fed a reaction composition comprising 0.049 wt % water, 0.27 wt % propylene glycol, 46.25 wt % ethyl levulinate, 53.05 wt % propylene glycol ketal of ethyl levulinate and 0.44 wt % of other impurities. The composition was fed into the first distillation column at a temperature between 90 to 110° C. at a rate of 60 to 80 lbs/hour. The overhead vacuum on the distillation column was 5 to 10 mm Hg. The mixture was refluxed in the column and recirculated in the bottom of the distillation column in a reboiler at a temperature of 100 to –130° C. The composition was then fed into a second distillation column at a temperature between 100 to 120° C. at a rate of 20 to 40 lbs/hour. The overhead vacuum on the column was 5 to 10 mm Hg. The mixture was refluxed in the column and recirculated in the bottom of the distillation column in a reboiler at a temperature of 80 to 100° C., distilled overhead, and collected. During the distillation, the bottoms of the distillation column were purged out at a rate of 3 lbs/hour. The final composition of the distilled product comprised 45 ppm water, 34 ppm propylene glycol, 0.08 wt % ethyl levulinate, 99.9% propylene glycol ketal of ethyl levulinate, and 0.01% other impurities. Examples 31-33 were performed similarly to Ex. 30, except the feed compositions were different. All compositions are shown in the Table 5.

The data in Table 5 shows the composition of the feed flowing into the first distillation column, the feed composition flowing into the second distillation column, and the composition of the final distilled and collected product from the overheads of the second distillation column.

The mixture was refluxed in the column and recirculated to the bottom of the distillation column in the reboiler at a temperature of 160 to 175° C. The composition was subsequently fed into a second distillation column at a temperature of 140 to 160° C. at a rate of 30 to 35 lbs/hour. The overhead vacuum on the column was 4 to 10 mm Hg. The mixture was refluxed in the column and recirculated in the bottom of the distillation column in the reboiler at a temperature of 170 to 180° C., distilled overhead and collected into a stainless steel container. The bottoms of the distillation column were purged at a rate of 2 to 4 lbs/hour. The final

TABLE 5

| Example | Feed Composition into 1st Distillation Column | | | | | Feed Composition into 2nd Distillation Column | | | | | Distillate from 2nd Distillation Column | | | | |
|---|---|---|---|---|---|---|---|---|---|---|---|---|---|---|---|
| | Et-LEV (%) | PG (ppm) | $H_2O$ (ppm) | Other Impurities (%) | I (%) | Et-LEV (ppm) | PG (ppm) | $H_2O$ (ppm) | Other Impurities (%) | I (%) | Et-LEV (ppm) | PG (ppm) | $H_2O$ (ppm) | Other Impurities (%) | I (%) |
| Example 28 | 37.7 | 7874 | 1015 | 0.55 | 60.9 | 1200 | 0 | 2 | 2.1 | 97.8 | 12100 | 4430 | 243 | 0.01 | 98.3 |
| Example 29 | 33.8 | 6125 | 758 | 0.55 | 65.0 | 300 | 0 | 12 | 1.56 | 98.4 | 8500 | 3073 | 179 | 0.2 | 98.6 |
| Example 30 | 46.3 | 2705 | 486 | 0.44 | 53.10 | 700 | 0 | 2 | 0.74 | 99.19 | 800 | 34 | 45 | 0.01 | 99.9 |
| Example 31 | 50.5 | 2406 | 395 | 0.35 | 48.90 | 600 | 0 | 10 | 0.78 | 99.17 | 900 | 50 | 112 | 0.03 | 99.9 |
| Example 32 | 45.9 | 2984 | 512 | 0.43 | 53.40 | 700 | 0 | 34 | 0.71 | 99.23 | 800 | 33 | 76 | 0.01 | 99.9 |
| Example 33 | 35.6 | 8251 | 982 | 0.6 | 62.80 | 400 | 0 | 15 | 0.88 | 99.09 | 1150 | 250 | 261 | 0.01 | 99.8 |

PG = propylene glycol
Et-Lev = ethyl levulinate

The data in the Table 5 shows that the final purity of the distilled composition of propylene glycol ketal of ethyl levulinate was greater than 99%, when the bottom, non-distilled fractions were purged from the bottom of the second distillation column. Examples 28 and 29 had non-detectable propylene glycol and less than 1500 ppm ethyl levulinate in the feed composition entering into the second distillation column. However, upon distilling the composition, the ethyl levulinate increased by 10-fold and the propylene glycol increased by more than 1000-fold. This indicated that while still achieving purity greater than 98%, the process for achieving a purity of greater than 99% is not as easily controlled.

However, purging the bottoms of the second distillation column during the distillation surprisingly resulted in only a very small increase in ethyl levulinate and propylene glycol in the final distilled product relative to the feed composition. This process therefore allows the production of greater than 99% pure propylene glycol ketal of ethyl levulinate product and a more consistent process.

Examples 34-38

The method used to synthesize glycerol ketal of ethyl levulinate described in Example 7 was used, except that the catalyst used was CSA in an amount of 50 to 500 ppm instead of sulfuric acid. The reaction proceeded to greater than 90% conversion, and glycerol ketal of ethyl levulinate was purified according to the following details. The compositions for Examples 34-38 are shown in the Table 6 below.

Into a packed bed of dibasic solid sodium phosphate was fed a reaction composition shown in Table 6 (Example 35) at a temperature of 70 to 110° C. and at a flow rate of 70 to 90 lbs/hour. The composition was fed into the first distillation column at a temperature between 90 to 110° C. at a rate of 70 to 90 lbs/hour. The overhead vacuum on the distillation column was 5 to 10 mm Hg.

composition of the distilled product is shown in Table 6 below. The acid number of the final distilled product was 0.01.

Example 37 was conducted in the same manner as Example 1 except that the catalyst used was CSA in an amount of 50 to 500 ppm instead of sulfuric acid and a packed bed of dibasic sodium phosphate was used prior to distillation. The acid number was 0.01.

Example 38 was the same as Example 7. The acid number was 0.01.

The compositions of Examples 34 and 36 were manufactured by a method used to synthesize the propylene glycol ketal of ethyl levulinate and the glycerol ketal of ethyl levulinate as described in Examples 1 and 7. The reaction proceeded to greater than 90% conversion, and propylene glycol ketal of ethyl levulinate was purified as detailed below. Into a middle zone of a distillation column was fed the reaction composition shown in the Table 6.

The composition was fed into the first distillation column at a temperature between 90 to 110° C. at a rate of 40 to 50 lbs/hour. The overhead vacuum on the distillation column was 5 to 10 mm Hg. The mixture was refluxed in the column and recirculated in the bottom of the distillation column in a reboiler at a temperature of 150 to 160° C. The composition was subsequently fed into a second distillation column at a temperature between 130 to 140° C. at a rate of 30 to 35 lbs/hour. The overhead vacuum on the column was 4 to 8 mm Hg. The mixture was refluxed in the column and recirculated in the bottom of the distillation column in a reboiler at a temperature of 170 to 180° C., distilled overhead, and collected into a stainless steel container. The final composition of the distilled product is shown in Table 6. The acid number of the final product of Example 34 was 0.28.

The acid number of the final product of Example 36 was 0.24.

The data in Table 6 shows the composition of the feed flowing into the first distillation column, the feed composition flowing into the second distillation column, and the composition of the final distilled and collected product from the overheads of the second distillation column.

may be adjusted from more acidic to more basic depending on the ratios of the reagents in the buffer solution.

TABLE 6

| | Feed Composition into 1st Distillation Column | | | | | | Feed Composition into 2nd Distillation Column | | | | Distillation from 2nd Distillation Column | | | |
|---|---|---|---|---|---|---|---|---|---|---|---|---|---|---|
| Example | Et-LEV (%) | Glycerol or PG (ppm) | Catalyst | Other Impurities (%) | Ketal (%) | Ketal Type | Et-LEV (%) | Glycerol or PG (ppm) | Other Impurities (%) | Ketal (%) | Et-LEV (%) | Glycerol or PG (ppm) | Other Impurities (%) | Ketal (%) |
| Example 34 | 47 | 1300 | $H_2SO_4$ | 1.94 | 50.9 | 8 | 0.12 | 500 | 13.9 | 86 | 0.22 | 2000 | 1.21 | 98.4 |
| Example 35 | 36.6 | 17000 | CSA | 1.1 | 60.6 | 8 | n/d | n/d | 2.1 | 97.9 | n/d | 800 | 0.04 | 99.9 |
| Example 36 | 48.3 | 8000 | $H_2SO_4$ | 0.1 | 50.8 | 7 | 0.1 | n/d | 1 | 98.8 | 0.3 | 100 | 0 | 99.6 |
| Example 37 | 49.7 | 2700 | $H_2SO_4$ | 0.2 | 49.9 | 7 | 0.1 | n/d | 0.7 | 99.2 | 0.1 | 500 | 0 | 99.8 |
| Example 38 | 44 | 18700 | CSA | 0.5 | 53.7 | 7 | 0.11 | n/d | 0.7 | 99.2 | 0.08 | n/d | 0.1 | 99.8 |

The data in Table 6 shows that the use of camphor sulfonic acid and the use of dibasic sodium phosphate or barium carbonate prior to distillation has surprisingly advantageous effects on the composition of the final ketal products. The final ketal products display less reformation of the starting materials, especially the ethyl levulinate. The preclusion of ethyl levulinate is advantageous because it is known to cause color problems, and it is not as stable to basic or reducing environments. Also it should be noted, that glycerol is removed in Example 35 to non-detectable levels in the first distillation column. This was surprising since it was known to distill at nearly the same temperature as the glycerol ketal of ethyl levulinate.

Examples 39

Example 38 was repeated as Example 39 except that propylene glycol derived from nature (via the hydrogenolysis of glycerol) was reacted with ethyl levulinate to produce the propylene glycol ketal of ethyl levulinate. The product composition was similar to that of Example 38.

Example 40-43

Examples 40-43 demonstrate the use of the materials of the present invention in a buffer system to provide stability.

Example 40

500 ppm (by weight) of glycerol ketal of ethyl levulinate made according to Example 35 in buffer was prepared by weighing 25 milligrams (mg) of glycerol ketal of ethyl levulinate into 50 grams of buffer solution (citrate buffer; pH 5). The solution was homogeneous in nature. The pH was stable over a period of more than 10 days.

Example 41

500 ppm (by weight) glycerol ketal of ethyl levulinate made according to Example 35 in buffer was prepared by weighing 25 mg of the glycerol ketal of ethyl levulinate into 50 grams of buffer solution (carbonate buffer; pH 9). The solution was homogeneous in nature. The pH was stable over a period of more than 10 days.

Buffers were prepared by making 0.1 molal (m) solutions of citric acid, sodium citrate, sodium carbonate and sodium bicarbonate. For the citrate buffer, 30.5 grams of 0.1 m citric acid was weighed and brought to 100 grams with 0.1 m sodium citrate for a pH 5. For the carbonate buffer 10 grams of 0.1 m sodium carbonate was weighed and brought to 100 grams with 0.1 m sodium bicarbonate for a pH 9. The pH Example 42

500 ppm (by weight) propylene glycol ketal of ethyl levulinate made according to Example 38 in buffer was prepared by weighing 25 mg of propylene glycol ketal of ethyl levulinate into 50 grams of buffer solution (citrate buffer; pH 5). The solution was homogeneous in nature. The pH was stable over a period of more than 10 days.

Example 43

500 ppm (by weight) propylene glycol ketal of ethyl levulinate made according to Example 38 in buffer was prepared by weighing 25 mg of propylene glycol ketal of ethyl levulinate into 50 grams of buffer solution (carbonate buffer; pH 9). The solution was homogeneous in nature. The pH was stable over a period of more than 10 days.

Example 44

Composition 8 (767.21 g) made according to Example 7 and 10% Pd on Carbon catalyst (0.7382 g) were added to a 1 L Parr reactor vessel. The reactor was purged with nitrogen. Hydrogen gas was then added to the reactor vessel to a pressure of 100 psi and the temperature was set to 140° C. The contents of the reactor were stirred continuously while the temperature of 140° C. and pressure of 115-120 psi was held for 6 hours. After 6 hours, the reaction mixture was allowed to cool to ambient temperature and the pressure was equilibrated to atmospheric. The contents of the flask were filtered to remove the Pd catalyst.

A sample was taken from the flask and analyzed by UV-VIS for the Index of Absorption Units (IAU), HPLC, and by GC-FID. The initial and final compositions are shown in Table 7.

Example 45

Composition 8 (793.66 g) made according to Example 7 and 10% Pd on Carbon catalyst (0.0803 g) was added to the 1 L Parr reactor vessel. The oxygen in the reactor was evacuated by purging with nitrogen gas until the oxygen level was under 1%. The reactor was then filled with nitrogen gas to 20 psi and held overnight to test for any leaks. After the reactor proved to hold pressure, hydrogen gas was purged into the reactor. Again any possible leaks were checked for before continuing with the reaction. Hydrogen gas was then added to the reactor vessel to a pressure of 100 psi and the temperature was set to 140° C. The contents of the reactor were stirred continuously while the temperature of 140° C. and pressure of 80-110 psi was held for 4 hours. The contents of Example 45 were then placed under hydrogenation conditions for a second time. The reactor was again tested for leaks under the same process as stated in Example 45 due to falling pressures. After the reactor proved to hold pressure and hydrogen gas was purged into the reactor, the hydrogen gas was then added to the reactor vessel to a pressure of 100 psi and the temperature was set to 140° C. The contents of the reactor were stirred continuously while the temperature of 140° C. and pressure of 80-110 psi was held for 3.25 hours. After 3.25 hours, the reaction mixture was allowed to cool to ambient temperature and the pressure was equilibrated to atmospheric. The contents of the flask were filtered to remove the Pd catalyst. A sample was taken from the flask and found that the IAU went from 0.031 to 0.000.

Examples 46-50

Similar hydrogenation reactions were performed according to the procedure in Example 44. The reaction conditions such as temperature, time, pressure, amount of catalyst, and type of hydrogenation catalyst varied and are listed in Table 7 along with HPLC and IAU results.

TABLE 7

| Example | Hydrogenated Material | Catalyst | Temp. (° C.) | Pressure (psi) | Time (hrs) | IAU Index | HPLC Impurity A % Change (230 nm, 37-38 min) | HPLC Other Impurities % Change (258 nm, 38-40 min) |
|---|---|---|---|---|---|---|---|---|
| 44 initial | 8 | 0.1% Pd | 140 | 120 | 6 | 0.031 | — | — |
| 44 final | | | | | | 0.000 | −80.24 | −23.35 |
| 45 initial | 8 | 0.01% Pd | 140 | 100 | 4 | 0.031 | — | — |
| 45 final | | | | | | 0.000 | — | — |
| 46 initial | 8 | 0.01% Pd | 140 | 630 | 4.5 | 0.000 | — | — |
| 46 final | | | | | | 0.023 | −80.24 | −23.35 |
| 47 initial | 8 | 0.1% Ni | 140 | 540 | 5 | 0.125 | — | — |
| 47 final | | | | | | 0.011 | −100.00 | −37.54 |
| 48 initial | 8 | 0.1% Ru | 140 | 530 | 5.5 | 0.000 | — | — |
| 48 final | | | | | | 0.000 | −84.62 | −4.92 |
| 49 initial | 7 | 0.1% Ni | 140 | 530 | 4 | 0.062 | — | — |
| 49 final | | | | | | 0.000 | — | — |
| 50 initial | 8 | 0.1% Ni | 200 | 500 | 4 | 0.125 | — | — |
| 50 final | | | | | | 0.064 | −100.00 | 16.56 |

Example 51

Celite was added to a 20 mL syringe up to the 5 mL line of the syringe. The syringe was attached to a 0.4 μm filter. Composition 8 (5 mL) made according to Example 7 was heated to 40° C. and added to the same 20 mL syringe on top of the Celite. The composition 8 was pushed through the plug of Celite by a plastic syringe plunger and the filtered liquid was analyzed by HPLC.

Examples 52

Following the same process as in Example 51, a variety of adsorbents and ion exchange resins were tested for color body removal in composition 8 made according to Example 7 (Examples 52-57). The HPLC results are listed in Table 8.

TABLE 8

| Example | Treatment | HPLC Color Body 1% Change (230 nm, 37-38 min) | HPLC Other Color Bodies % Change (258 nm, 38-40 min) |
|---|---|---|---|
| 51 | Celite | −1.92 | −2.12 |
| 52 | Carbon (Norit) | −29.82 | −26.39 |
| 53 | Alumina | 41.75 | −100.00 |
| 54 | Amberlyst A-26 | 19.67 | −87.03 |
| 55 | Amberlyst A-21 | −63.60 | −86.57 |
| 56 | Amberlite XAD-2 | −42.31 | −47.71 |
| 57 | NaBH4 + Norit | 0.00 | −94.60 |

Example 58

Composition 8 (75 mL) made according to Example 7 and household bleach (40 mL) were added to a 250 mL beaker and mixed at room temperature. The contents were poured into a separatory funnel and allowed to separate overnight. The composition 8 was extracted from the separatory funnel and analyzed. The HPLC and IAU results are listed in Table 9.

TABLE 9

| Example | Treatment | HPLC Other Color Bodies % Change (258 nm, 38-40 min) | Initial IAU Index | Final IAU Index |
|---|---|---|---|---|
| 58 | bleach | −100.00 | 0.000 | 0.079 |

Example 59-62

Composition 8 made according to Example 7 and 0.2% Tinuvin 833, a UV stabilizer, were added to a glass vial. The sample and stabilizer were mixed until dissolved on a hot plate. The vial containing the sample and stabilizer were placed in a UV chamber, open to the atmosphere. The IAU index was recorded over time and given in Table 10.

TABLE 10

| Ex. # | UV aged Material | 0 hr IAU Index | 24 hr IAU Index | 48 hr IAU Index | 3 day IAU Index | 4 day IAU Index | 5 day IAU Index | 6 day IAU Index | 14 day IAU Index | 21 day IAU Index | UV agent (%) | Heat Stabilizer (%) | Other |
|---|---|---|---|---|---|---|---|---|---|---|---|---|---|
| 59 | Alumina-treated 8 | 0.0 | — | — | — | — | 0.00 | — | — | — | — | — | — |
| 60 | Hydrogenated 8 (Ru catalyst) | 0 | — | — | — | — | 0.016 | — | — | — | — | — | — |
| 61 | Hydrogenated 8 (Ni catalyst) | 0.0 | — | — | — | — | 0.00 | — | — | — | — | — | — |
| 62 | Hydrogenated 7 | 0.0 | — | — | — | — | 0.505 | — | — | — | — | — | — |

Example 63

Composition 8 made according to Example 7 was added to a 250 mL flask equipped with stir-bar, thermocouple, and an inlet and outlet for nitrogen. The contents were dried by heating with a heating mantle overnight at 65° C. under nitrogen purge. A sample was taken from the flask, and the water content in the flask was measured to be less than 100 ppm using Karl Fischer analysis. The temperature was then set to 230° C. and held constant for 4 hrs. The IAU index results are shown in Table 11.

Example 64

Composition 7 made according to Example 1 was added to a 250 mL flask equipped with stir-bar, thermocouple, and an inlet and outlet for nitrogen. The contents were dried by heating with a heating mantle overnight at 65° C. under nitrogen purge. A sample was taken from the flask, and the water content in the flask was measured to be less than 100 ppm using Karl Fischer analysis. The temperature was then set to 230° C. and held constant for 4 hrs.
The IAU index results are shown in Table 11.

TABLE 11

Thermo Stability Initial and Final IAU results for Examples 83-112

| Example | Heated Material | Conditions | Initial IAU Index | Final IAU Index |
|---|---|---|---|---|
| 63 | 8 | 230 C. 4 hrs | 0.040 | 0.165 |
| 64 | 7 | 230 C. 4 hrs | 0.082 | 0.458 |

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The endpoints of all ranges directed to the same component or property are inclusive of the endpoint and independently combinable. The term "comprising" is inclusive of the transition terms "consisting of" and "consisting essentially of".

Unless otherwise defined, all terms (including technical and scientific terms) used herein have the same meaning as commonly understood by one of ordinary skill in the art to which this invention belongs.

The compounds made by the above-described methods have, in embodiments, one or more isomers. Where an isomer can exist, it should be understood that the invention embodies methods that form any isomer thereof, including any stereoisomer, any conformational isomer, and any cis, trans isomer; isolated isomers thereof; and mixtures thereof.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. Alkyl groups may be straight-chained or branched. Throughout the specification, reference is made to various bivalent groups. Such groups are the same as the monovalent groups that are similarly named, and are typically indicated with an "ene" suffix. For example, a C1 to C6 alkylene group is a bivalent linking group having the same structure as a C1 to C6 alkyl group.

All cited patents, patent applications, and other references are incorporated herein by reference in their entirety.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for the manufacture of a propylene glycol ketal of ethyl levulinate, the method comprising:
   contacting propylene glycol with ethyl levulinate and an acid catalyst in a reactor under reaction conditions to produce a first product that comprises a propylene glycol ketal of ethyl levulinate;
   fractionating the first product under fractionation conditions to separate fractionated materials from the first product to produce a second product that comprises less than 1000 parts per million of propylene glycol;
   recycling the fractionated materials back to the reactor; and distilling the second product under distillation conditions in a distillation column to produce a third product comprising the propylene glycol ketal of ethyl levulinate and less than or equal to about 2 wt % contaminants; wherein the contaminants comprise one or more of acid species, ethyl levulinate, water, or a high molecular weight byproduct comprising high molecular weight species having molecular weights that are at least 1.5 times greater than the molecular weight of the propylene glycol ketal of ethyl levulinate, wherein the reactor is a continuous multistage reactor comprising a first reactor, a second reactor and a third reactor, and the method comprises contacting the propylene glycol with the ethyl levulinate and the acid catalyst in the first reactor under a first set of reaction conditions to produce a product from the first reactor that comprises the propylene glycol ketal of ethyl levulinate:

continuously sending the product from the first reactor to the second reactor that is downstream of the first reactor and subjecting the product from the first reactor to a second set of reaction conditions to provide a product from the second reactor; and continuously sending the product from the second reactor to the third reactor that is downstream of the second reactor and subjecting the product to a third set of reaction conditions to provide the first product.

2. The method of claim 1, wherein the high molecular weight byproduct is one or more of dimers, trimers or oligomers produced by a reaction between one or more of the propylene glycol ketal of ethyl levulinate, ethyl levulinate, propylene glycol, and/or an aldol of the propylene glycol ketal of ethyl levulinate or produced by a reaction between the propylene glycol ketal of ethyl levulinate and itself.

3. The method of claim 1, wherein the third product comprises less than 200 ppm water, less than 20 ppm acid, less than or equal to about 10,000 ppm of propylene glycol, less than or equal to about 0.25 wt % of dimers obtained from a reaction between monomers of the propylene glycol ketal of ethyl levulinate, less than or equal to about 0.25 wt % of dimers obtained from a reaction between the propylene glycol ketal of ethyl levulinate and an aldol of the propylene glycol ketal of ethyl levulinate, less than or equal to about 0.25 wt % of dimers obtained from a reaction between the propylene glycol ketal of ethyl levulinate and ethyl levulinate, less than or equal to about 0.1 wt % of trimers obtained from a reaction between the propylene glycol ketal of ethyl levulinate, ethyl levulinate and aldols of propylene glycol ketal of ethyl levulinate and less than or equal to about 0.10 wt % of trimers obtained from a reaction between the propylene glycol ketal of ethyl levulinate and ethyl levulinate, where the weight percents are based on the total weight of the third product.

4. The method of claim 1, wherein the ethyl levulinate is added to the reactor in a stoichiometric excess relative to the propylene glycol.

5. The method of claim 1, wherein a molar ratio of ethyl levulinate to propylene glycol is between about 5:1 to about 1:5.

6. The method of claim 1, further comprising subjecting the first product to an acid removal column to remove the acid catalyst, an organic acid formed form the contacting, or a combination thereof prior to the fractionation.

7. The method of claim 1, further comprising purging the distillation column to remove the high molecular weight species.

8. The method of claim 1, where the reaction conditions comprise a temperature between about 50 and 150° C.

9. The method of claim 1, where the reaction conditions comprise a pressure of between about 5 and 760 millimeters of mercury.

10. The method of claim 1, wherein:
the fractionated materials are separated from the first product in a first distillation column and the propylene glycol ketal of ethyl levulinate is separated from the high molecular weight species in a second distillation column, wherein the first reactor, the second reactor, the third reactor, the first distillation column and the second distillation columns are in fluid communication with each other.

11. The method of claim 10, wherein the first reactor, the second reactor, the third reactor, the first distillation column and the second distillation column are in series.

12. The method of claim 10, where the first distillation column or the second distillation column is purged to remove acid species or the high molecular weight species.

13. The method of claim 1, further comprising passing the first product through a bed of inorganic base or buffer prior to fractionation.

14. The method of claim 13, where the base is a carbonate, an amine, a hydroxide, a phosphate or an oxide.

15. The method of claim 13, where the buffer comprises a packed bed of inorganic salt.

16. The method of claim 13, where the buffer comprises a solution of citric acid, sodium citrate, sodium carbonate, sodium bicarbonate, sodium phosphate, calcium phosphate, or a combination comprising at least one of the foregoing buffers.

17. The method of claim 1, wherein the catalyst is a heterogeneous catalyst.

18. The method of claim 1, wherein the catalyst is a homogeneous catalyst.

19. A method for the manufacture of a propylene glycol ketal of ethyl levulinate, the method comprising:
contacting propylene glycol with ethyl levulinate and an acid catalyst in a reactor under reaction conditions to produce a first product that comprises a propylene glycol ketal of ethyl levulinate;
fractionating the first product under fractionation conditions to separate fractionated materials from the first product to produce a second product that comprises less than 1000 parts per million of propylene glycol;
recycling the fractionated materials back to the reactor; and
distilling the second product under distillation conditions in a distillation column to produce a third product comprising the propylene glycol ketal of ethyl levulinate and less than or equal to about 2 wt % contaminants; wherein the contaminants comprise one or more of acid species, ethyl levulinate, water, or a high molecular weight byproduct comprising high molecular weight species having molecular weights that are at least 1.5 times greater than the molecular weight of the propylene glycol ketal of ethyl levulinate,
wherein the acid catalyst is camphor sulfonic acid.

20. The method of claim 19, wherein a molar ratio of ethyl levulinate to propylene glycol is between about 5:1 to about 1:5.

21. The method of claim 19, further comprising subjecting the first product to an acid removal column to remove the acid catalyst, an organic acid formed form the contacting, or a combination thereof prior to the fractionation.

22. The method of claim 19, further comprising purging the distillation column to remove the high molecular weight species.

23. The method of claim 19, where the reaction conditions comprise a temperature between about 50 and 150° C., and a pressure of between about 5 and 760 millimeters of mercury.

24. The method of claim 19, further comprising passing the first product through a bed of inorganic base or buffer prior to fractionation.

25. The method of claim 19, wherein the catalyst is a homogeneous catalyst.

26. A method for the manufacture of a propylene glycol ketal of ethyl levulinate, the method comprising:
    contacting propylene glycol with ethyl levulinate and an acid catalyst in a reactor under reaction conditions to produce a first product that comprises a propylene glycol ketal of ethyl levulinate;
    fractionating the first product under fractionation conditions to separate fractionated materials from the first product to produce a second product that comprises less than 1000 parts per million of propylene glycol;
    recycling the fractionated materials back to the reactor; and
distilling the second product under distillation conditions in a distillation column to produce a third product comprising the propylene glycol ketal of ethyl levulinate and less than or equal to about 2 wt % contaminants; wherein the contaminants comprise one or more of acid species, ethyl levulinate, water, or a high molecular weight byproduct comprising high molecular weight species having molecular weights that are at least 1.5 times greater than the molecular weight of the propylene glycol ketal of ethyl levulinate, the method further comprising hydrogenating the third product.

27. The method of claim 26, wherein a molar ratio of ethyl levulinate to propylene glycol is between about 5:1 to about 1:5.

28. The method of claim 26, further comprising subjecting the first product to an acid removal column to remove the acid catalyst, an organic acid formed form the contacting, or a combination thereof prior to the fractionation.

29. The method of claim 26, further comprising purging the distillation column to remove the high molecular weight species.

30. The method of claim 26, where the reaction conditions comprise a temperature between about 50 and 150° C., and a pressure of between about 5 and 760 millimeters of mercury.

31. The method of claim 26, further comprising passing the first product through a bed of inorganic base or buffer prior to fractionation.

32. The method of claim 26, wherein the catalyst is a heterogeneous catalyst or a homogeneous catalyst.

33. The method of claim 26, wherein the catalyst is a homogeneous catalyst.

* * * * *